(12) United States Patent
Haruta et al.

(10) Patent No.: US 12,246,130 B2
(45) Date of Patent: Mar. 11, 2025

(54) MEDICINE DISPENSING DEVICE AND METHOD FOR MANUFACTURING SAME

(71) Applicant: Shin Nippon Biomedical Laboratories, Ltd., Kagoshima (JP)

(72) Inventors: Shunji Haruta, Kagoshima (JP); Genji Satoyoshi, Kagoshima (JP); Hideaki Mishima, Kagoshima (JP)

(73) Assignee: Shin Nippon Biomedical Laboratories, Ltd., Kagoshima (JP)

( * ) Notice: Subject to any disclaimer, the term of this patent is extended or adjusted under 35 U.S.C. 154(b) by 907 days.

(21) Appl. No.: 17/295,031

(22) PCT Filed: Oct. 2, 2019

(86) PCT No.: PCT/JP2019/038943
§ 371 (c)(1),
(2) Date: May 18, 2021

(87) PCT Pub. No.: WO2020/105290
PCT Pub. Date: May 28, 2020

(65) Prior Publication Data
US 2021/0393897 A1    Dec. 23, 2021

(30) Foreign Application Priority Data

Nov. 19, 2018 (JP) .................. 2018-216575
Jul. 9, 2019 (JP) .................. 2019-127425

(51) Int. Cl.
*A61M 15/08* (2006.01)
*A61M 11/02* (2006.01)
*A61M 15/00* (2006.01)

(52) U.S. Cl.
CPC ............ *A61M 15/08* (2013.01); *A61M 11/02* (2013.01); *A61M 15/0035* (2014.02); *A61M 15/0043* (2014.02); *A61M 2202/064* (2013.01)

(58) Field of Classification Search
CPC .................. A61M 15/08; A61M 11/02; A61M 2202/064; A61M 13/00; A61M 15/0035;
(Continued)

(56) References Cited

U.S. PATENT DOCUMENTS 5,776,125 A * 7/1998 Dudar .................. A61M 5/162
604/88
6,398,074 B1 * 6/2002 Bruna .................. B05B 11/062
222/386

(Continued)

FOREIGN PATENT DOCUMENTS

JP    S59-034267 A    2/1984
JP    H03-131271 A    6/1991
(Continued)

OTHER PUBLICATIONS

International Search Report for International Application No. PCT/JP2019/038943 (2 pages).

*Primary Examiner* — Kendra D Carter
*Assistant Examiner* — Mautin I Ashimiu
(74) *Attorney, Agent, or Firm* — Finnegan, Henderson, Farabow, Garrett & Dunner, LLP

(57) ABSTRACT

A device according to one aspect of the present invention is an intranasal powdered medicine dispensing device (10) for dispensing a predetermined dose of a powdered medicine into a nasal cavity. The device includes a nozzle member (20) that includes a filling space (22) for a powdered medicine (M) and an ejection opening (26) for the powdered medicine (M), a closing member that closes the ejection opening (26), a sealing member (40) that seals an opening (24) of the filling space (22), an injection pump member (50) that sends out air, as the injection pump member contracts, to eject the powdered medicine from the ejection opening (26), a puncturing member (60) that moves, as the injection pump member (50) contracts, and forms a hole by punctur- (Continued)

ing in the sealing member (40) while moving, and a guide member (70) that restricts the puncturing member (60) from moving in a direction perpendicular to the direction of the movement thereof.

17 Claims, 50 Drawing Sheets

(58) Field of Classification Search
CPC ............ A61M 15/0038; A61M 15/004; A61M 15/0041; A61M 11/006–008; B05B 11/0054; B05B 11/0038; B05B 11/007; B05B 11/0008; B05B 11/026; B05B 11/02; B05B 11/04; B05B 11/10
See application file for complete search history.

(56) References Cited

U.S. PATENT DOCUMENTS

| | | | |
|---|---|---|---|
| 6,866,039 B1* | 3/2005 | Wright | A61M 15/0028 222/321.6 |
| 2002/0092524 A1* | 7/2002 | Lockhart | B05B 11/062 128/203.21 |
| 2003/0047184 A1 | 3/2003 | Lockhart et al. | |
| 2004/0050885 A1* | 3/2004 | Stradella | A61M 15/0028 222/633 |
| 2006/0169278 A1* | 8/2006 | Djupesland | B05B 11/061 128/200.14 |
| 2008/0006269 A1 | 1/2008 | Lockhart et al. | |
| 2008/0177246 A1 | 7/2008 | Sullivan et al. | |
| 2008/0210229 A1* | 9/2008 | Corbacho | B05B 11/1092 128/200.22 |
| 2010/0192950 A1* | 8/2010 | Chopard | A61M 15/0051 128/203.15 |
| 2011/0045088 A1 | 2/2011 | Tsutsui et al. | |
| 2013/0158474 A1 | 6/2013 | Sullivan et al. | |
| 2015/0367366 A1 | 12/2015 | Edwards et al. | |

FOREIGN PATENT DOCUMENTS

| | | |
|---|---|---|
| JP | H10-179739 A | 7/1998 |
| JP | 2004-526480 A | 9/2004 |
| JP | 2010-515541 A | 5/2010 |

* cited by examiner

 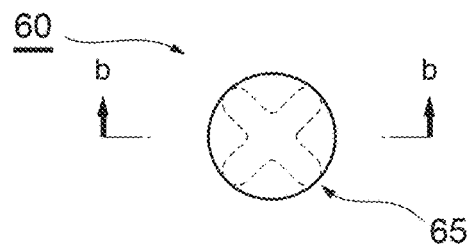
 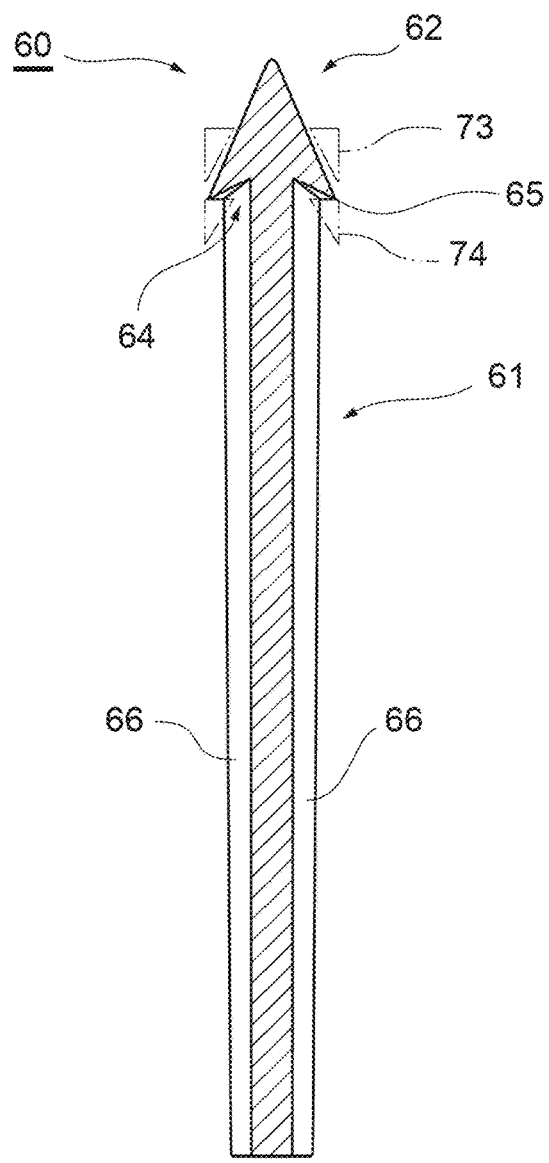
 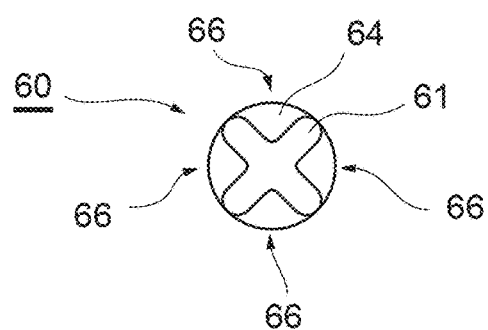

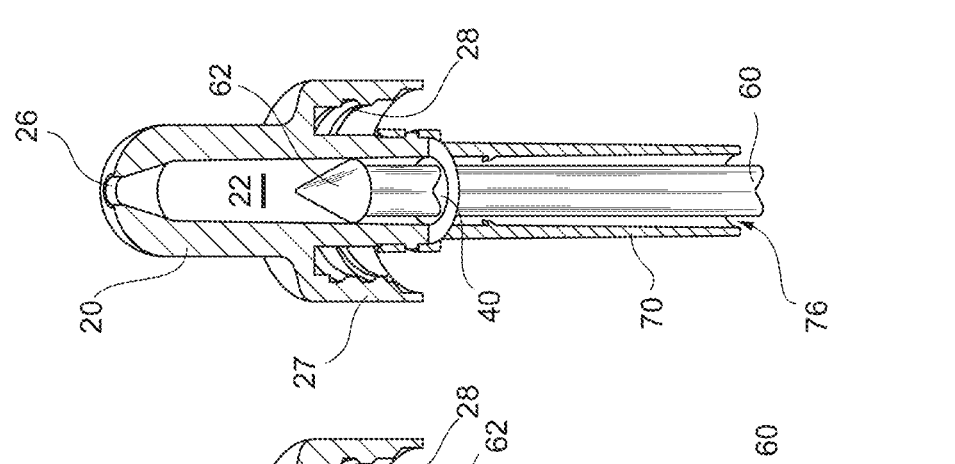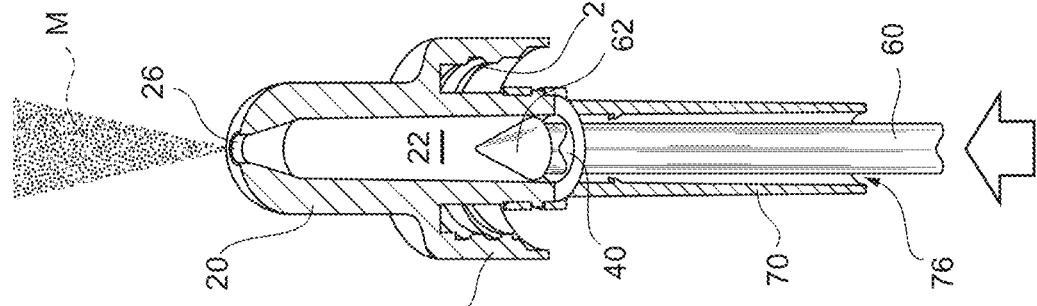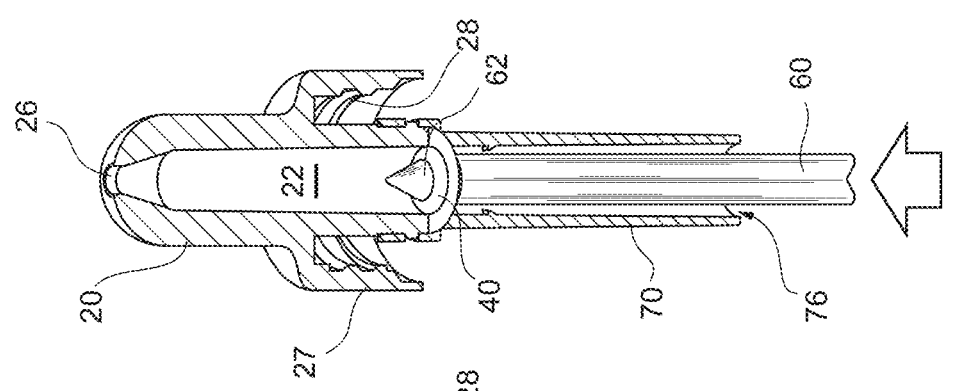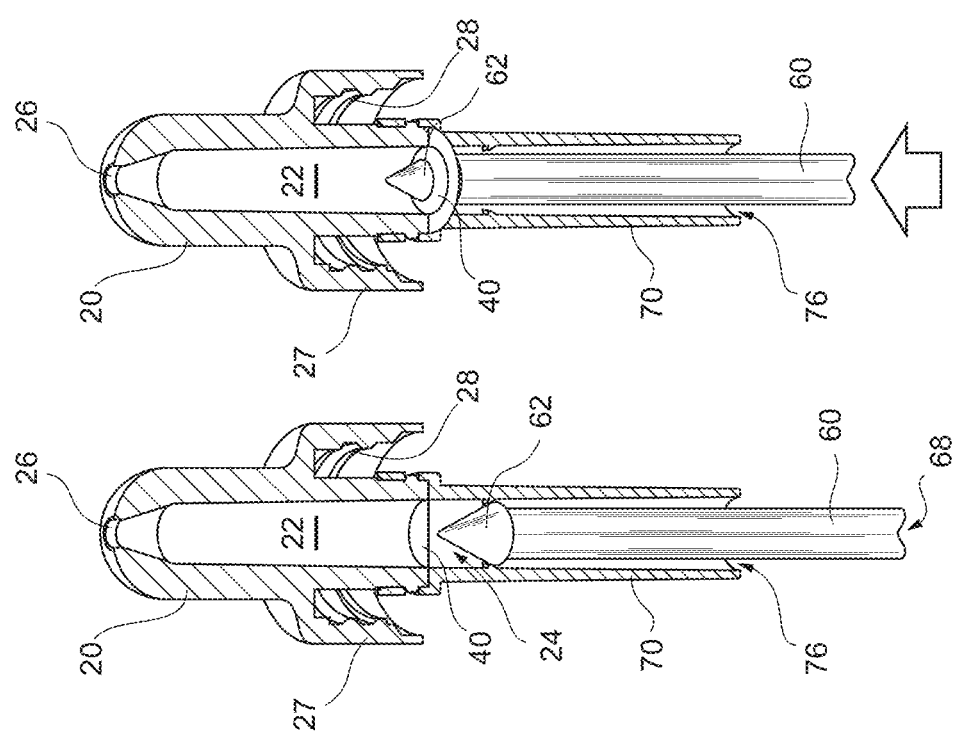
FIG. 15

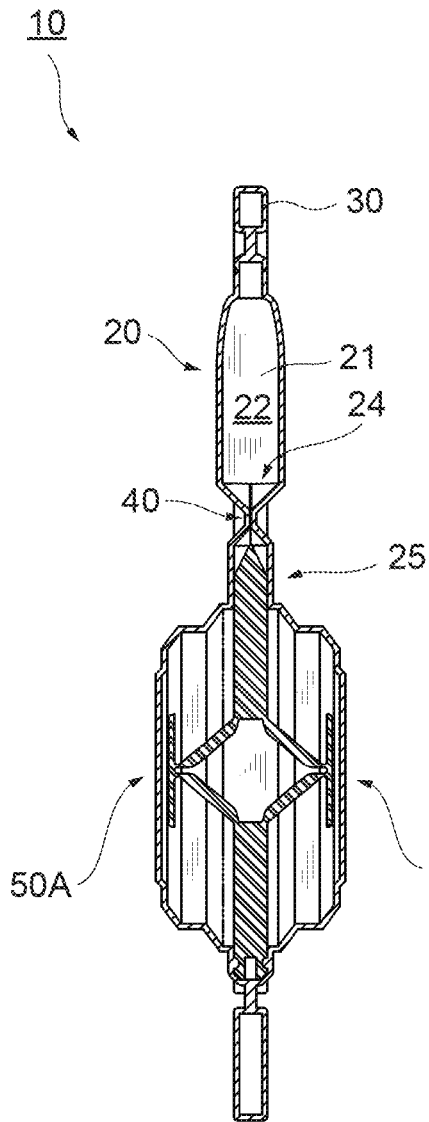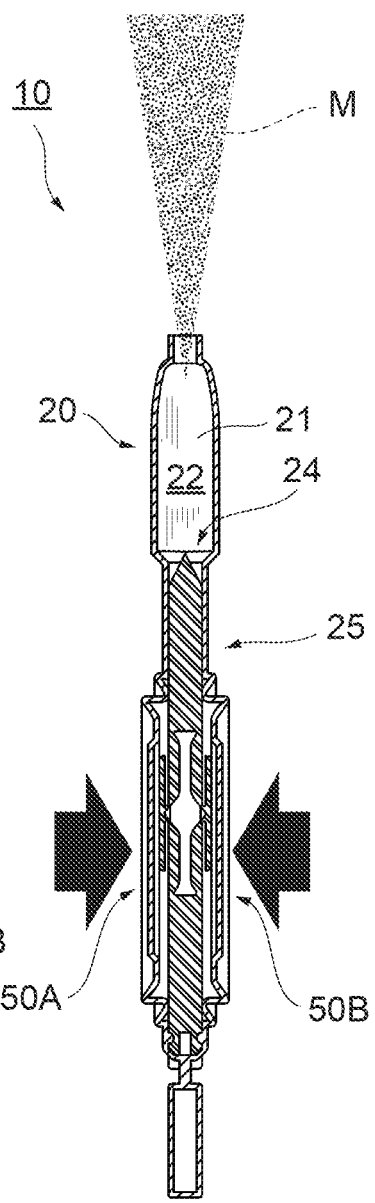
*Fig.42A*  *Fig.42B*

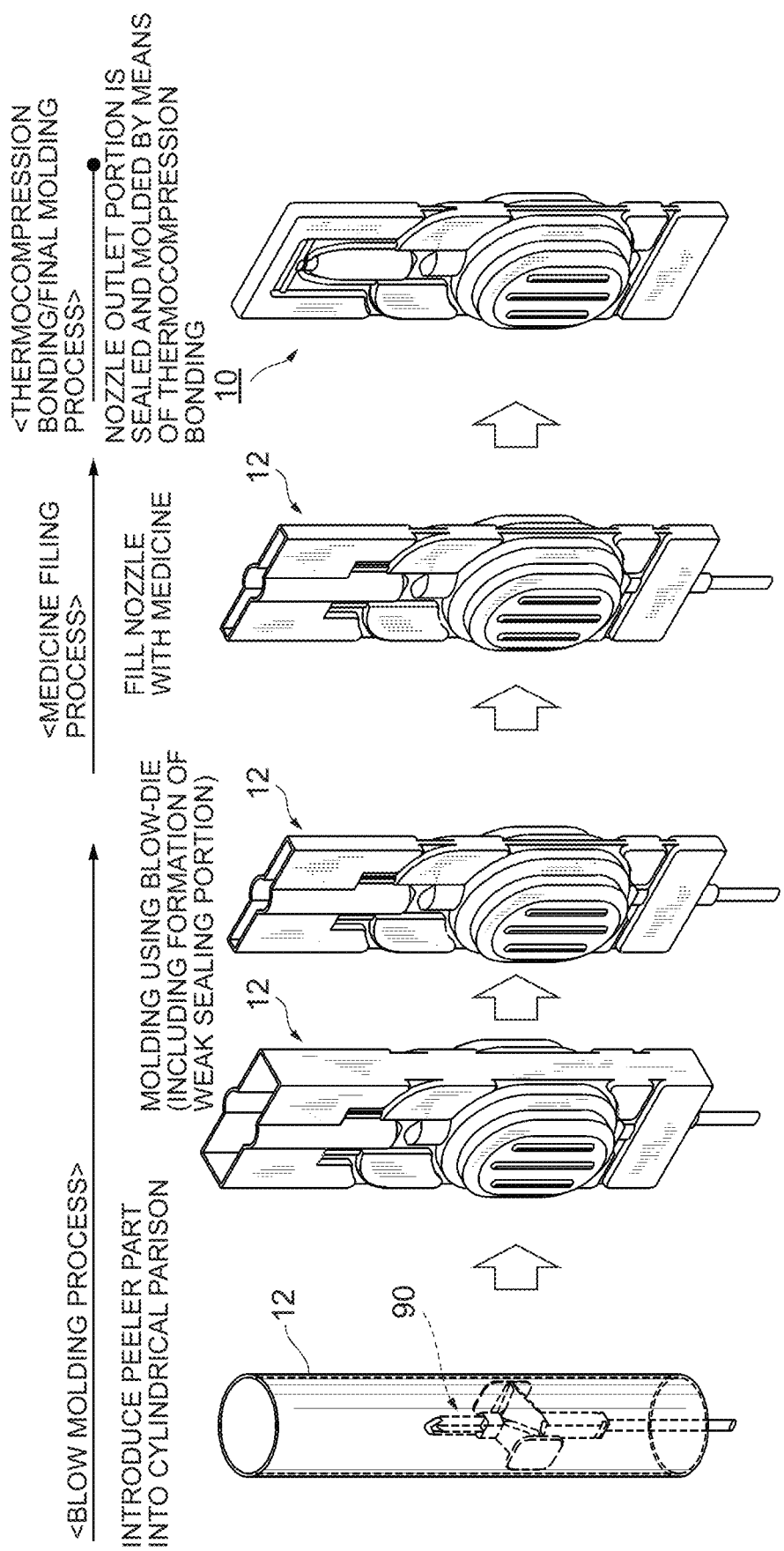

MEDICINE DISPENSING DEVICE AND METHOD FOR MANUFACTURING SAME

This application is a national stage filing under 35 U.S.C. § 371 of International Application No. PCT/JP2019/038943, filed on Oct. 2, 2019, and published as WO/2020/105290, which claims priority to Japanese Patent Application No. 2019-127425, filed on Jul. 9, 2019, and Japanese Patent Application No. 2018-216575, filed on Nov. 19, 2018. International Application No. PCT/JP2019/038943 is incorporated herein by reference in its entirety.

TECHNICAL FIELD

The present invention relates to a medicine dispensing device and a method for manufacturing the same, and more specifically to a structure and the like of a medicine dispensing device of a single-use type for dispensing a predetermined dose of a powdered medicine into a nasal cavity and the like.

BACKGROUND ART

A treatment in which a powdered medicine is dispensed into a nasal cavity of a patient with sinus infection, nasal allergy, or the like has been generally known. In this treatment, a powdered medicine filled in a capsule is dispensed into the nasal cavity by using a dedicated dispensing device. Also, a medicine dispensing device conventionally used in this treatment has been devised (see Patent Document 1, for example).

In the medicine dispensing device described in Patent Document 1, a pump portion is provided on the air inflow-side of a cylindrical member, a recessed portion into which a capsule is inserted is formed on the air outflow-side of the cylindrical member, a tip portion of the cylindrical member is fitted into this recessed portion to form a capsule accommodating portion, and an air introduction passage having a valve mechanism is formed so as to extend from this capsule accommodating portion to the pump portion. In addition, another valve mechanism is provided on the other side of the pump portion. By this valve mechanism and the valve mechanism provided in the air introduction passage, air is supplied to the capsule accommodating portion through the air introduction passage when the pump portion is pressed, and air is sucked into the pump portion from the outside when the pump portion is returned to an original state. The medicine dispensing device also includes a cap fitted into the tip portion of the cylindrical member and a needle extending axially inside this cap, and is configured such that holes are formed on both sides of the capsule in the axial direction by fitting the cap in a state in which the recessed portion of the cylindrical member and the tip portion having an opening are fitted together.

In the device with such configuration, in order to form the holes in the capsule, the capsule filled with a powdered medicine is inserted into the recessed portion of the cylindrical member, and then, the tip portion is fitted to insert the capsule into the capsule accommodating portion. Then, by fitting the cap into the tip portion made of a hard resin, the holes are formed in both axial ends of the capsule by the needle provided on the inside of the cap that is guided to the tip portion.

Next, in order to administer the medicine, the user removes the cap from the cylindrical member, inserts the tip portion into the nostril on one side, and presses the pump portion so that the air from the pump portion flows into the capsule through the air introduction passage, whereby the medicine in the capsule is delivered and dispensed into the nasal cavity of the user. The medicine is dispensed into both nasal cavities by repeating the operation following the insertion of the tip portion.

CITATION LIST

Patent Document

Patent Document 1: Patent Publication JP S59-34267A

SUMMARY

Technical Problem

However, none of the conventional nasal medicine dispensing devices has been improved from the viewpoints of (a) improving the uniformity of each dose, (b) improving the preservation of the medicine in a storage container, (c) simplifying the administration operation, and (d) improving portability.

Specifically, among the nasal medicine dispensing devices for dispensing powdered medicines, there are (i) a multi-dose administration device in which a plurality of doses of a medicine are collectively stored in a container inside the administration device, and one dose of the medicine is divided and administered in multiple doses from the container for each administration (see WO 2001/095962, for example), and (ii) a single-dose administration device in which a container such as a capsule or a cartridge containing a single dose of a medicine is loaded into the administration device for each administration (Patent Document 1 corresponds to this administration device). The (ii) single-dose administration device includes a device of a so-called disposable type in which the whole administration device can be discarded after use. The (i) multi-dose administration device is extremely useful in terms of portability and convenience because multiple doses of a medicine can be stored in a single administration device. However, this device involves a task of dividing one dose of the medicine into multiple doses, and if this task is not performed properly, the required precise dose of the medicine cannot be obtained through the dividing, and as a result, the required dose of the medicine may not be able to be stably administered every time, which means the multi-dose administration device is not suitable for the use of medicines that require strict dosage control. In addition, since it is extremely difficult to keep a container containing multiple doses of a medicine in a sealed state over the entire duration of use, if the medicine easily takes up moisture or easily becomes oxidized, the powdered medicine may become denatured or decomposed in the container during the duration of use. Furthermore, since the same nozzle is repeatedly used, the exterior of the nozzle may become soiled from nasal discharge or the medicine may stick and remain in the nozzle after administration, requiring regular cleaning of the nozzle. Therefore, the multi-dose administration device has issues relating to the accuracy of a dosage, ensured medicine stability, need for regular maintenance, and the like since the multi-dose administration device involves a rigorous task of obtaining the required dose of medicine through dividing every time, low sealability of the medicine storage container, requirement of regular cleaning of the nozzle, and the like.

On the other hand, an advantage of the (ii) single-dose administration device is that the container such as a capsule or a cartridge containing a single dose of a medicine is loaded into the administration device for each administration, enabling reliable administration of the required dose of the medicine every time. Moreover, since containers such as capsules and cartridges are individually packaged and can be sealed and stored until use, the single-dose administration device is relatively easily used for medicines that easily take up moisture or become oxidized. However, as with the device disclosed in Patent Document 1, a capsule is employed as the medicine container, and the task of loading the capsule into the administration device and removing the used capsule from the administration device after administration is required as a preparation performed at each administration. Further, in forming the holes at the top and bottom of the capsule using the needle as a preparation performed at each administration, the needle punctures the capsule and then is pulled out of the capsule in order to ensure an air vent, which means taking the needle in and out may cause fragments of the capsule to mix into the medicine. In addition, the positions on the capsule for forming the holes using the needle may not be steady every time, causing unstable injection of the medicine from the nozzle. In the device disclosed in Patent Document 1, for example, since the same nozzle is repeatedly used, the exterior of the nozzle may become soiled from nasal discharge or the medicine may stick and remain in the nozzle after administration, requiring regular cleaning of the nozzle. Therefore, the single-dose administration device has issues such as requiring tasks such as loading and removing the container containing a single dose of a medicine into and out of the administration device, forming holes by puncturing in the medicine container, and regular maintenance.

The conventional devices also include a problem where how the medicine is ejected changes depending on the operation performed at the time of administration, but none of the conventional devices have been improved from such a viewpoint.

Thus, an object of the present invention is to provide an intranasal delivery device for powdered medicine, which not only is capable of improving uniformity of each dose, improving the preservation of a medicine in a storage container, simplifying the administration operation, and improving portability, but also can solve other problems.

Solution to Problem

One aspect of the present invention is a medicine dispensing device of a single-use type for dispensing a predetermined dose of a powdered medicine into a nasal cavity, the medicine dispensing device comprising:
  a nozzle member that includes a filling space to be filled with a powdered medicine and an ejection opening from which the powdered medicine is ejected;
  a closing member that closes the ejection opening;
  a sealing member that seals an opening of the filling space; and
  an injection pump member that sends out air, as the pump member contracts, to eject the powdered medicine from the ejection opening.

Since the medicine dispensing device described above has the nozzle member that includes the filling space to be filled with a predetermined dose of a powdered medicine, the improvement in uniformity of each dose can easily be realized by, preferably, filling the filling space with a single dose of the medicine. In addition, the present invention can specialize in implementation in which a single dose of a medicine is used up at once, making it easier to achieve improvement in portability by reducing the size and weight of the device. In other words, the nozzle member can be caused to function as a container for a powdered medicine (with a single dose), achieving a structure that can easily realize the improvement of dose uniformity and portability.

Furthermore, adopting the implementation in which a single dose of a medicine is used up at once can overcome the hygiene problems due to the repetitive use of the nozzle, such as the need to clean the nozzle when the nozzle becomes soiled from nasal discharge or the like after repetitive use of the nozzle, and administration of a denatured or decomposed medicine remaining in the nozzle into the body.

In addition, in the medicine dispensing device described above, preferably, by filling the nozzle member with a single dose of the medicine in advance and sealing the nozzle member containing the medicine until use, the medicine dispensing device can not only solve problems that may occur in association with medical efficacy and toxicity relating to storage stability in the medicine container (problem that the medicine dispensing device is not suitable for medicines that are easily decomposed or denatured due to humidity, oxygen, etc.), but also improve the preservation of the medicine.

The medicine dispensing device described above can particularly favorably be applied to medicines that easily take up moisture or become oxidized, by adopting a configuration in which a sealing space is formed in the nozzle member by sealing the opening of the nozzle member with a sealing member, and a puncturing member forms a hole by puncturing in the sealing member as the powdered medicine is ejected.

In the medicine dispensing device described above, it is preferred that a tip portion of the puncturing member have a tapered shape for facilitating forming the hole by puncturing.

In the medicine dispensing device described above, on a rear side of the tip portion of the puncturing member, a cap portion may be formed to direct part of air, flowing into the filling space through the hole, to outside in a radial direction.

In the medicine dispensing device described above, the cap portion may be inclined to approach gradually the tip portion from outside toward inside in the radial direction.

In the medicine dispensing device described above, in a part other than the tip portion of the puncturing member, a groove portion extending along a direction of movement may be formed.

The medicine dispensing device described above may further include a puncturing member that moves, as the injection pump member contracts, and forms a hole by puncturing in the sealing member during the movement, and a guide member that restricts the puncturing member from moving in a direction perpendicular to the direction of the movement of the puncturing member.

In the medicine dispensing device described above, a base end portion of the puncturing member may be in contact with a bottom portion of the pump member.

In the medicine dispensing device described above, the pump member may have a tapered shape and narrow down from the nozzle member side toward the bottom portion of the pump member.

The medicine dispensing device described above may be provided with a finger hook portion, on which a user can hook his/her finger when the user causes the pump member to contract.

In the medicine dispensing device described above, the pump member may have an oval cross section or an elliptical cross section.

In the medicine dispensing device described above, the pump member may also be provided with a pump malfunction prevention cover that prevents malfunction caused by an erroneous operation performed on the pump member.

The medicine dispensing device described above may further include a return motion prevention member that prevents the pump member from returning to an original state thereof after contracting.

In the medicine dispensing device described above, the pump member may be configured not to be able to easily return to an original shape thereof after contracting.

The medicine dispensing device described above may be configured in such a manner that sealing of the sealing member is released when a positive pressure is applied.

In the medicine dispensing device described above, a sealing force of the sealing member applied to the opening of the filling space may be set within a range in which the sealing member peels in the middle of an internal pressure rise, which is caused by the contraction of the pump member.

The sealing member of the medicine dispensing device described above may be formed by thermocompression bonding of a part of a flow passage between the nozzle member and the pump member.

The medicine dispensing device described above may further include an unsealing member that operates according to an operation by the user and releases the sealed state of the opening.

The unsealing member of the medicine dispensing device described above may be a member that elongates as the pump member contracts, and comes into contact with the sealing member during the elongation to release a sealed state of the opening.

The unsealing member of the medicine dispensing device described above may be composed of a member that pushes forward from the pump member side to the nozzle member side beyond the sealing member and releases the sealed state.

A tip of the unsealing member of the medicine dispensing device described above may be provided with a groove to make rectification.

The medicine dispensing device described above may further include a guide member that restricts the unsealing member from moving in a direction perpendicular to the direction of the elongation of the unsealing member.

The pump member of the medicine dispensing device described above may have a shape that expands in a direction perpendicular to a direction in which the medicine is ejected from the nozzle member.

The unsealing member of the medicine dispensing device described above may be built into the pump member.

The unsealing member of the medicine dispensing device described above may include a pair of plate-like pressed portions.

The unsealing member of the medicine dispensing device may be provided with an erroneous operation suppressing member that suppresses the pump member from contracting due to an erroneous operation.

In the medicine dispensing device described above, the unsealing member may be made of a plastic material that does not easily return to an original shape thereof after being deformed.

The unsealing member of the medicine dispensing device described above may be partially heat-welded to the pump member.

The unsealing member of the medicine dispensing device described above may be heat-welded to the pump member at a base end portion of the unsealing member on an opposite side thereof to the ejection opening.

The tip portion of the unsealing member of the medicine dispensing device described above may have a tapered shape.

The unsealing member of the medicine dispensing device described above may be composed of a member that is installed inside the pump member and releases the sealed state of the sealing member by enlarging the sealing member.

One aspect of the present invention is a method for manufacturing the medicine dispensing device described above, comprising the steps of molding the unsealing member by injection molding, and molding an outer portion of the unsealing member by blow molding, injection molding, or vacuum molding.

Advantageous Effects of Invention

The present invention can provide an intranasal delivery device for powdered medicine that not only is capable of improving uniformity of each dose, improving the preservation of a medicine in a storage container, simplifying the administration operation, and improving portability, but also can solve other problems.

BRIEF DESCRIPTION OF DRAWINGS

FIG. 10A shows a plan view of the piercer.
FIG. 10B shows a vertical cross-sectional view of the piercer, taken along line b-b of FIG. 10A.
FIG. 10C shows a bottom view of the piercer.

FIG. 15 is a perspective view of a vertical cross sectional showing operations of the piercer and the like performed for dispensing the powdered medicine M in the chronological order T from (A) to (D).

FIG. 42A shows a cross-sectional view of the intranasal delivery device for powdered medicine (medicine dispensing device) according to a sixth embodiment of the present invention.

FIG. 42B shows a cross-sectional view of the intranasal delivery device for powdered medicine during or after activation thereof.

FIGS. 58A to 58E are drawings for sequentially explaining steps taken place when blow molding the intranasal delivery device for powdered medicine.

DESCRIPTION OF EMBODIMENTS

Figure 1:
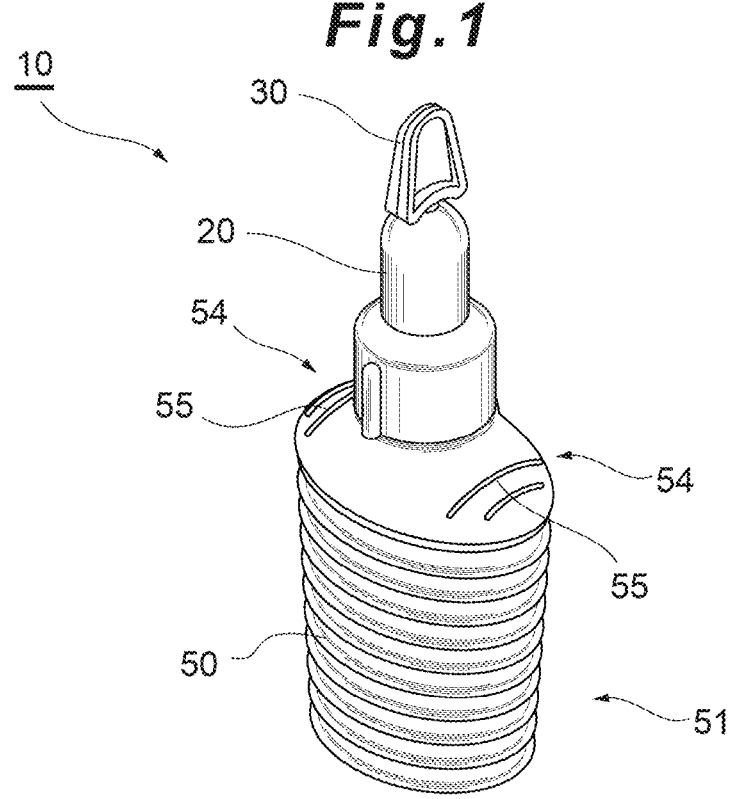
FIG. 1 is a perspective view showing the appearance of an intranasal delivery device for powdered medicine (intranasal powdered medicine dispensing device) according to one embodiment of the present invention.

Configurations of the present invention are now described hereinafter in detail on the basis of the embodiments shown in the drawings.

First Embodiment

<Configuration Example of Intranasal Delivery Device for Powdered Medicine>

An intranasal powdered medicine dispensing device (also called "intranasal delivery device for powdered medicine", hereinafter) 10 is a favorable device for single use, to dispense a predetermined dose of a powdered medicine into a nasal cavity of a patient. The intranasal delivery device for powdered medicine 10 of the present embodiment includes a nozzle member 20, a tab 30, a sealing member 40, a pump member 50, a piercer 60, a guide member 70, and the like (see FIGS. 1 to 4 and the like).

The nozzle member 20 has a tapered shape so as to facilitate the administration of a powdered medicine into a nasal cavity of a patient, and is provided with an appropriate level of roundness in the vicinity of a tip as necessary (see FIG. 15 and the like). A filling space 22 that is filled with the powdered medicine is formed inside the nozzle member 20 (see FIG. 14 and the like). An ejection opening 26 for ejecting a powdered medicine M is provided at the center of the tip of the nozzle member 20 (see FIGS. 2, 14, and the like). An opening 24 through which the filling space 22 can be filled with the powdered medicine M, and an annular cap portion 27 are formed on a base end side of the nozzle member 20 (the side of the nozzle member 20 attached to the pump member 50 side) (see FIGS. 14, 15, and the like). A thread portion 28 for attaching the nozzle member 20 to the pump member 50 is formed on an inner peripheral surface of the annular cap portion 27 (see FIG. 14(A)).

The tab 30 is a member (closing member) for closing the ejection opening 26 of the nozzle member 20. The tab 30 of the present embodiment is attached to the tip of the nozzle member 20 in a breakable manner, and at the time of use, a user (also referred to as "user") breaks off the tab 30 with a hand to open the ejection opening 26 (see FIGS. 1, 2, and the like).

Figure 3A:
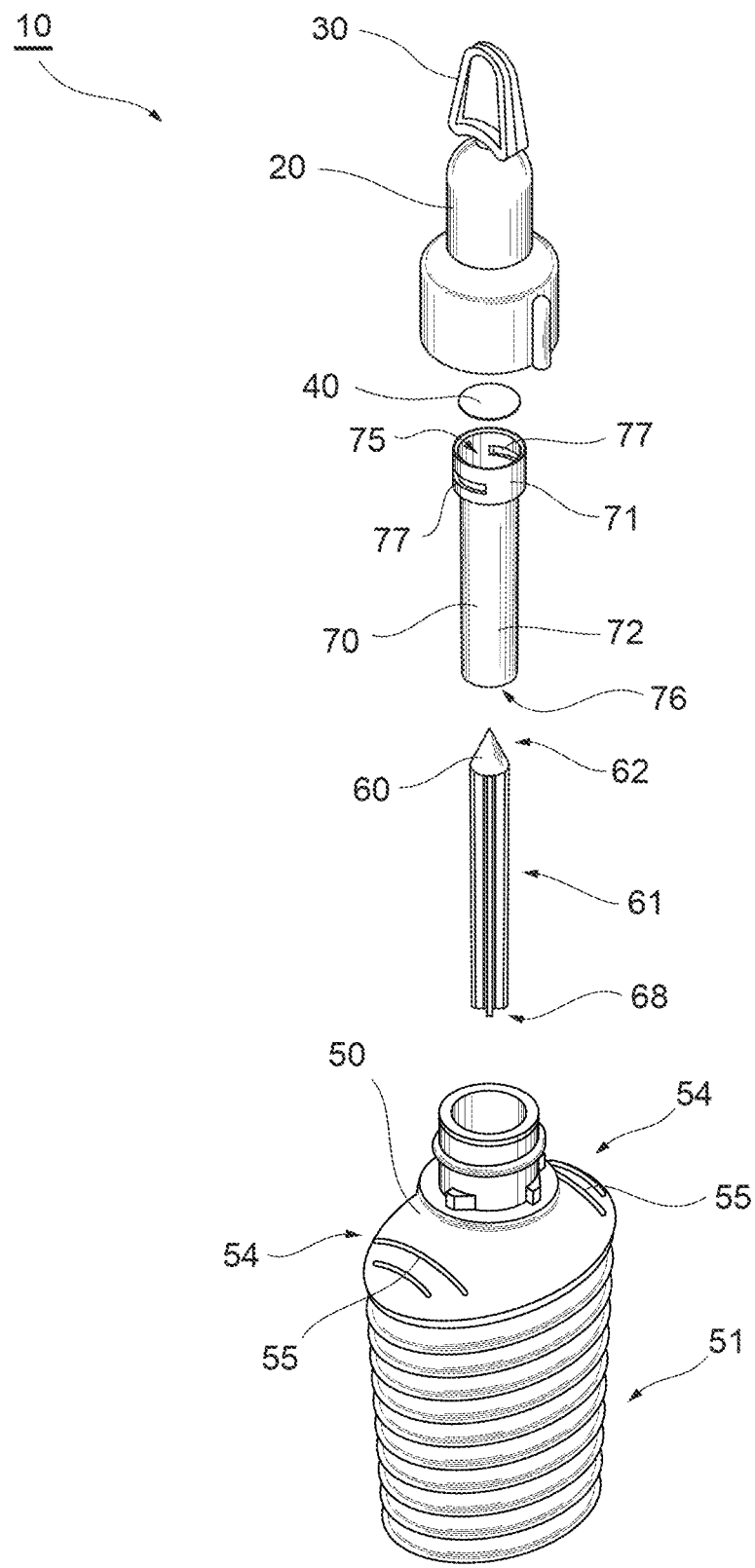
FIG. 3A is an exploded perspective view of the intranasal delivery device for powdered medicine.
Figure 3B:
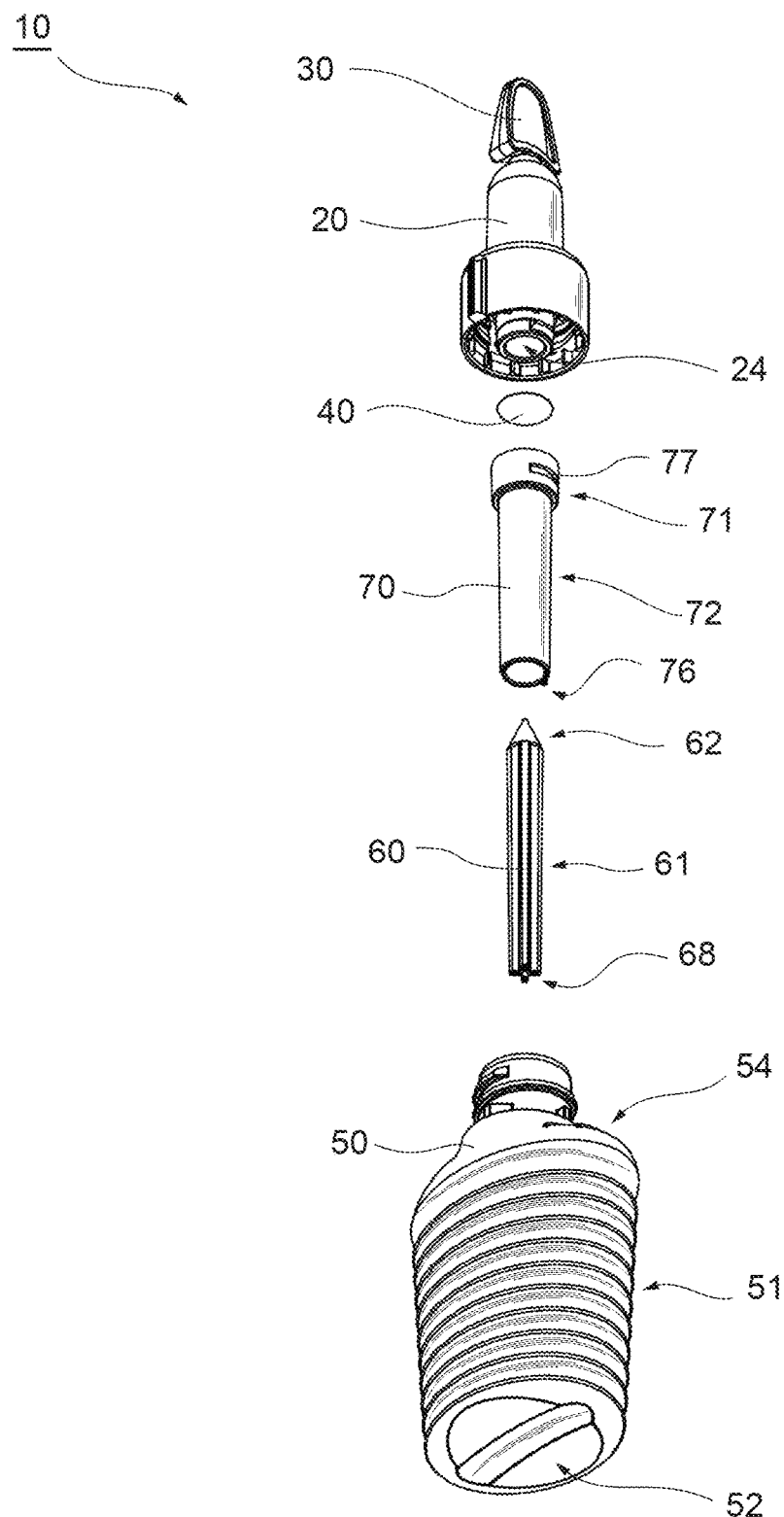
FIG. 3B is an exploded perspective view showing the intranasal delivery device for powdered medicine from a bottom surface side.
Figure 3C:
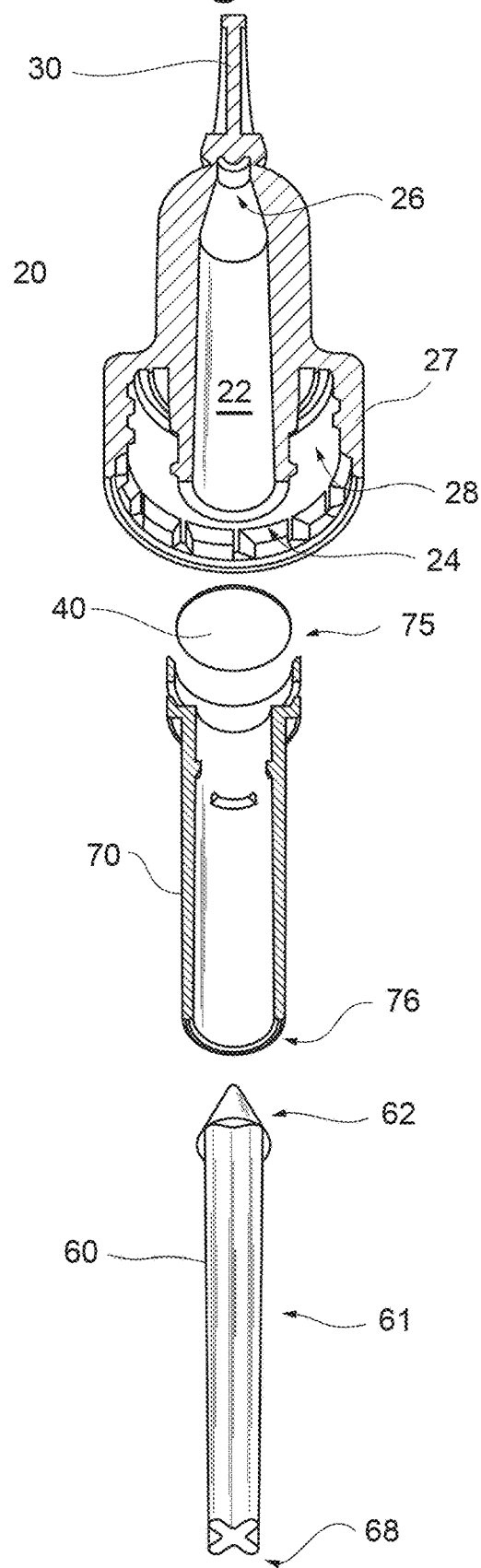
FIG. 3C is an exploded perspective view of vertical cross sections of a nozzle member, a tab, a sealing member, a holder (guide member), and a piercer (puncturing member) that are shown in FIG. 3B (except for the sealing member and the piercer).
Figure 4:
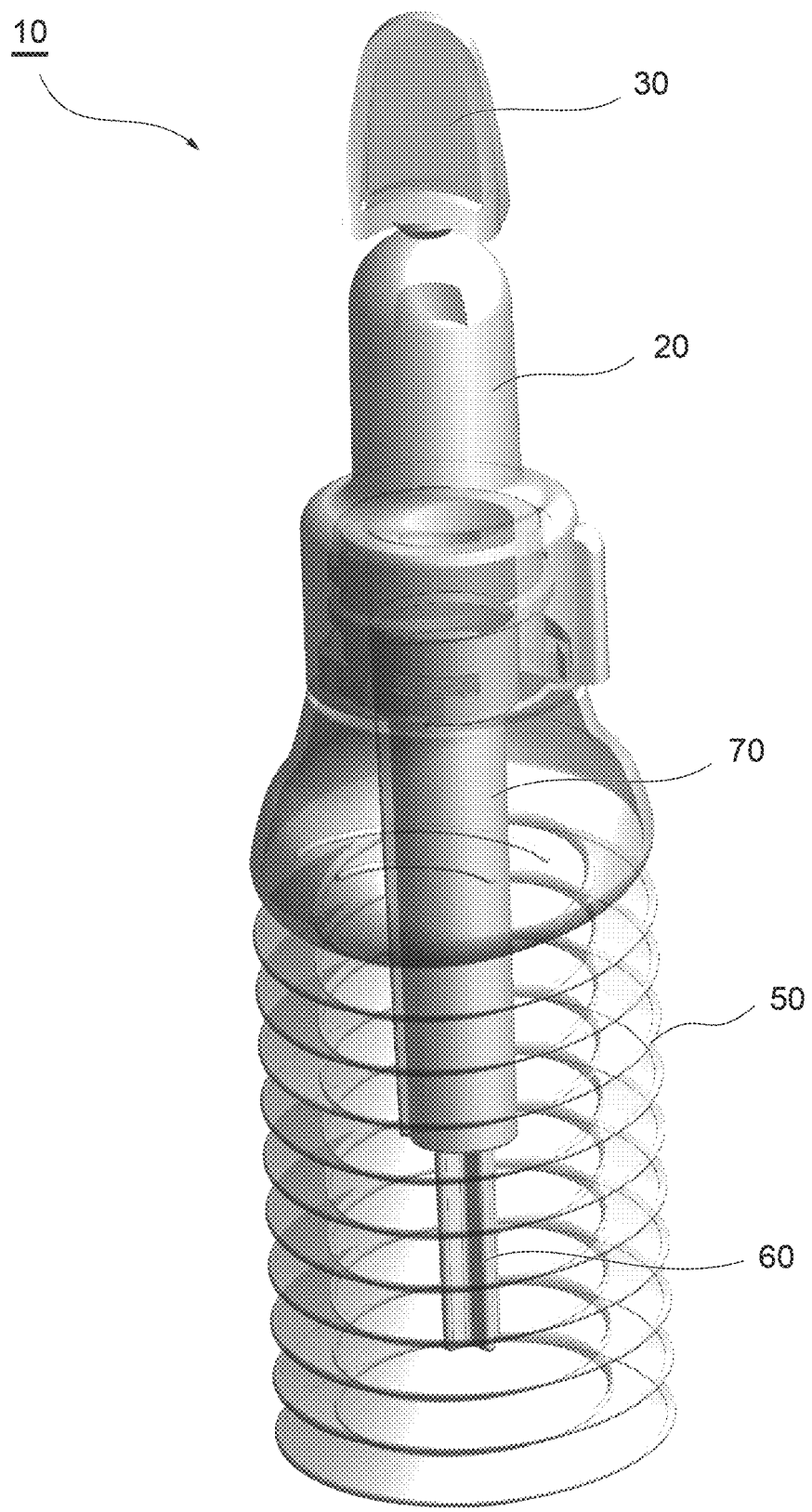
FIG. 4 is a perspective view showing a configuration of the entire intranasal delivery device for powdered medicine, in which the nozzle member and a pump member of the device are transparent or translucent.
Figure 5:
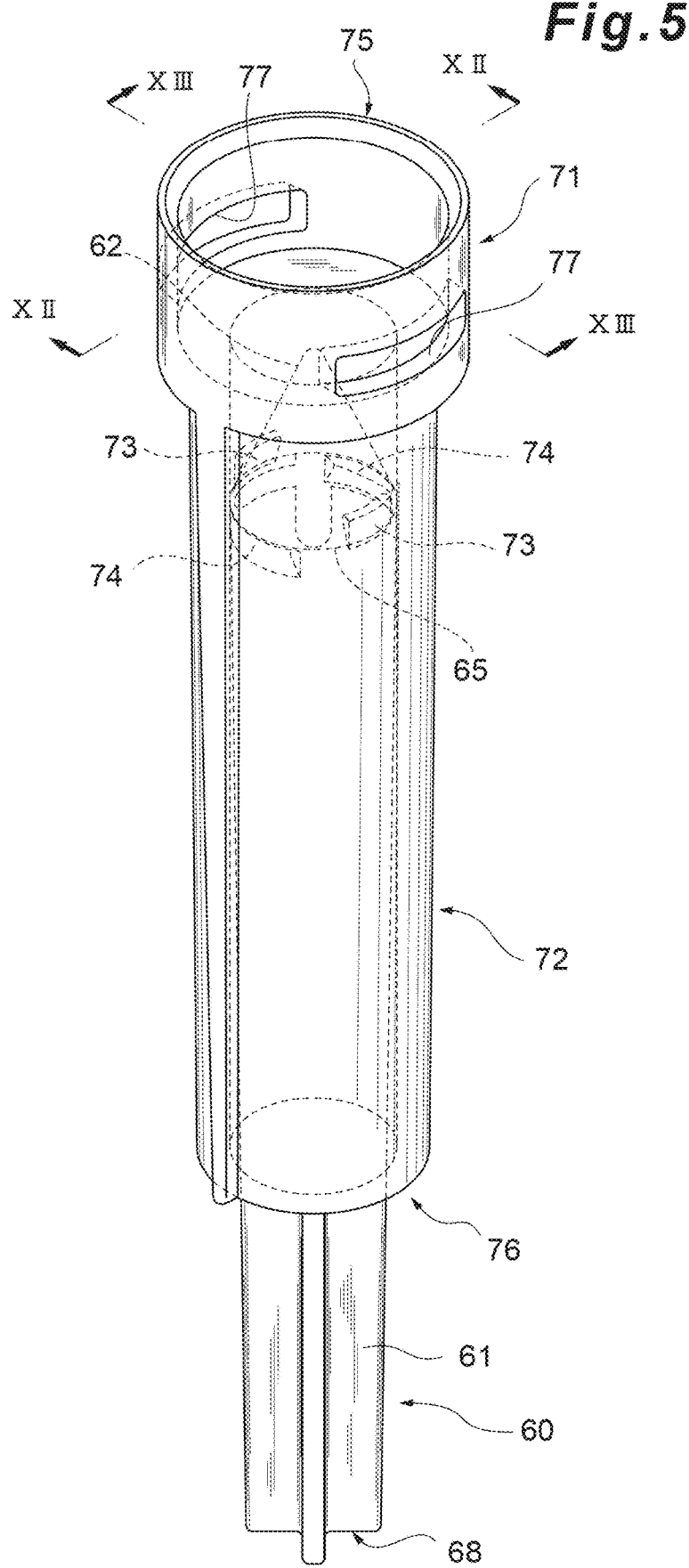
FIG. 5 is a perspective view showing a configuration example of the holder (guide member) and the piercer (puncturing member).

The sealing member 40 is a member for sealing the opening 24 of the filling space 22 of the nozzle member 20 (see FIGS. 3B, 3C, and the like). It is preferred that a moisture-proof film or the like that not only seals the filling space 22 to prevent the powdered medicine M from being deteriorated by air or moisture but also can easily be punctured with the piercer 60, be used as the sealing member 40. The present embodiment adopts the sealing member 40 that maintains airtightness without tearing or peeling even when an internal pressure of the pump member 50 rises to a predetermined level.

The pump member 50 is a member that feeds air to eject the powdered medicine M from the ejection opening 26 of the nozzle member 20 when the intranasal delivery device for powdered medicine 10 is being used. In the present embodiment, a member having a structure in which a bellows portion 51 contracts when the user pushes a bottom portion 52 with a finger is adopted as the pump member 50 (see FIG. 4 and the like).

Figure 14:
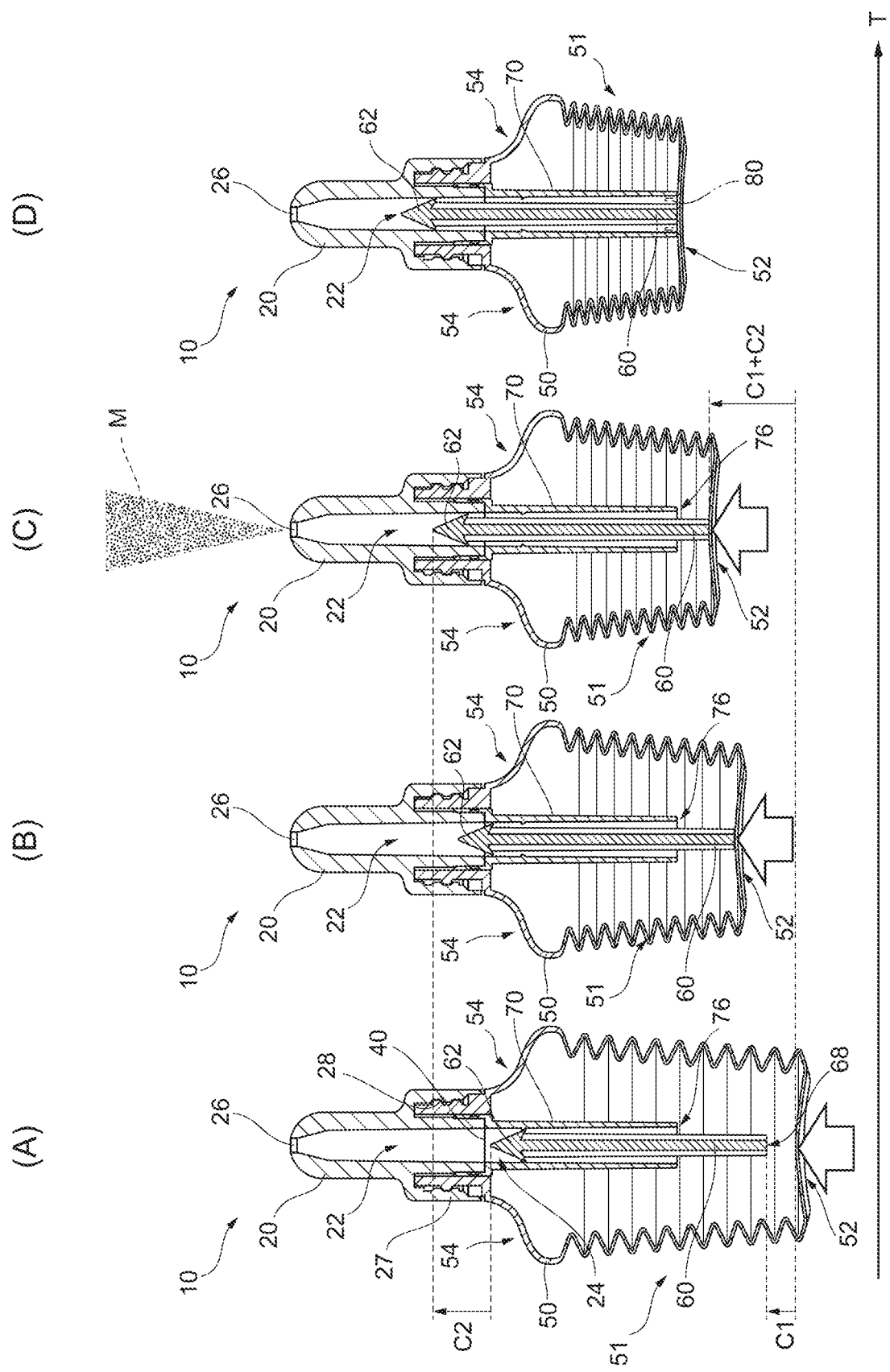
FIG. 14 is a vertical cross-sectional view showing operations of the intranasal delivery device for powdered medicine that are performed for dispensing a powdered medicine M, in chronological order T from (A) to (D).

Specific shapes of the pump member 50 are not particularly limited, but the present embodiment employs, for example, a tapered cross-sectional shape for the pump member 50 in which the pump member 50 tapers from the nozzle member 20 side toward the bottom portion 52 (see FIG. 14 and the like). In order to efficiently produce ejection air from a small pump, it is important to form the pump into a shape that allows easy contraction (easy collapse) and to utilize the air corresponding to the internal volume of the pump as the injection air as much as possible. When the pump member 50 has such a tapered shape, the overlap between the peaks of the bellows portion 51 obtained when the pump member 50 contracts gradually changes, allowing the pump to easily contract efficiently while the reaction force of the pump (the force of the pump trying to return to the original shape thereof) is small. Therefore, even with such a small pump, the user can create injection air with a small force. Also, if the bottom portion 52 is narrow, the position where the user puts his/her thumb during use is likely to be uniform, and as a result, when the pump member 50 contracts, the bottom portion 52 is prevented from moving to the left and right, thereby stabilizing the contraction. Thus, an advantage is obtained in which the variation in contraction for each user is less likely to occur.

A finger hook portion 54 that is shaped to allow the user such as a patient (including a doctor or the like who administers the medicine to the patient) to put his/her finger easily thereon, especially an index finger and a middle finger, is formed on each shoulder portion of the pump member 50 (see FIG. 14 and the like). By hooking the index finger and the middle finger on the respective left and right finger hook portions 54, the user can easily push the bottom portion 52 with his/her thumb to cause the pump member 50 to contract. A surface of each finger hook portion 54 may be provided with roughness or the like that functions as a non-slip portion 55 to suppress the fingers from slipping (see FIG. 2 and the like).

Figure 2:
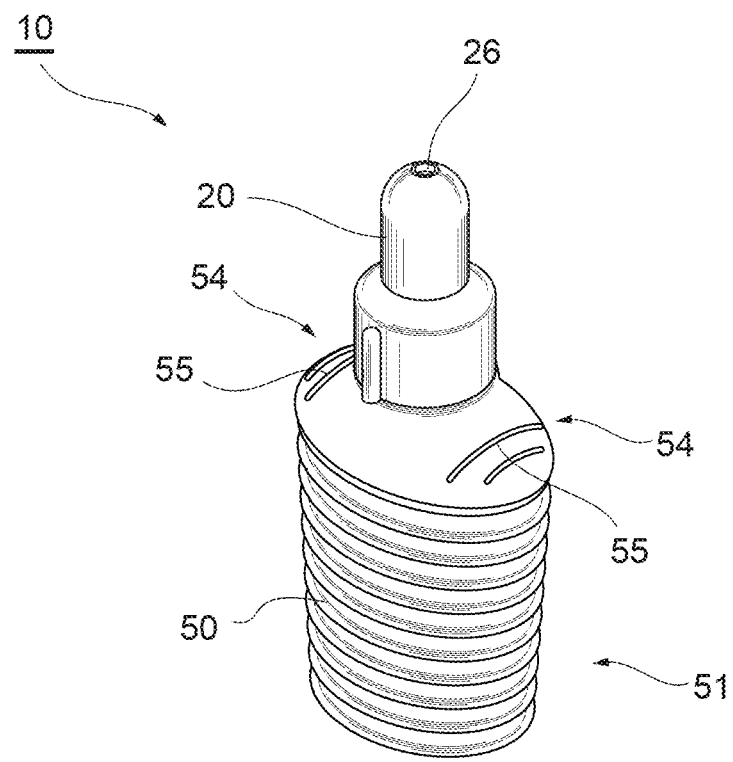
FIG. 2 is a perspective view showing the appearance of the intranasal delivery device for powdered medicine having a tab to be broken off for use.

The cross-sectional shape of the pump member 50 is not also limited and may be, for example, circular, but in the present embodiment, an oval or elliptic cross-sectional shape that collapses in one direction is employed (see FIG. 2 and the like).

The piercer 60 is a member that moves as the pump member 50 contracts, and forms a hole by puncturing in the sealing member 40 while moving. The piercer 60 of the present embodiment includes a shaft portion 61, a tip portion 62 facing the nozzle member 20 side, and a base end portion 68 that is pressed when the pump member 50 contracts. The tip portion 62 has a shape that enables easy formation of a hole by puncturing in the sealing member 40, such as a conical shape that tapers from an edge portion 65 toward the tip (see FIG. 14 and the like).

Figure 11:
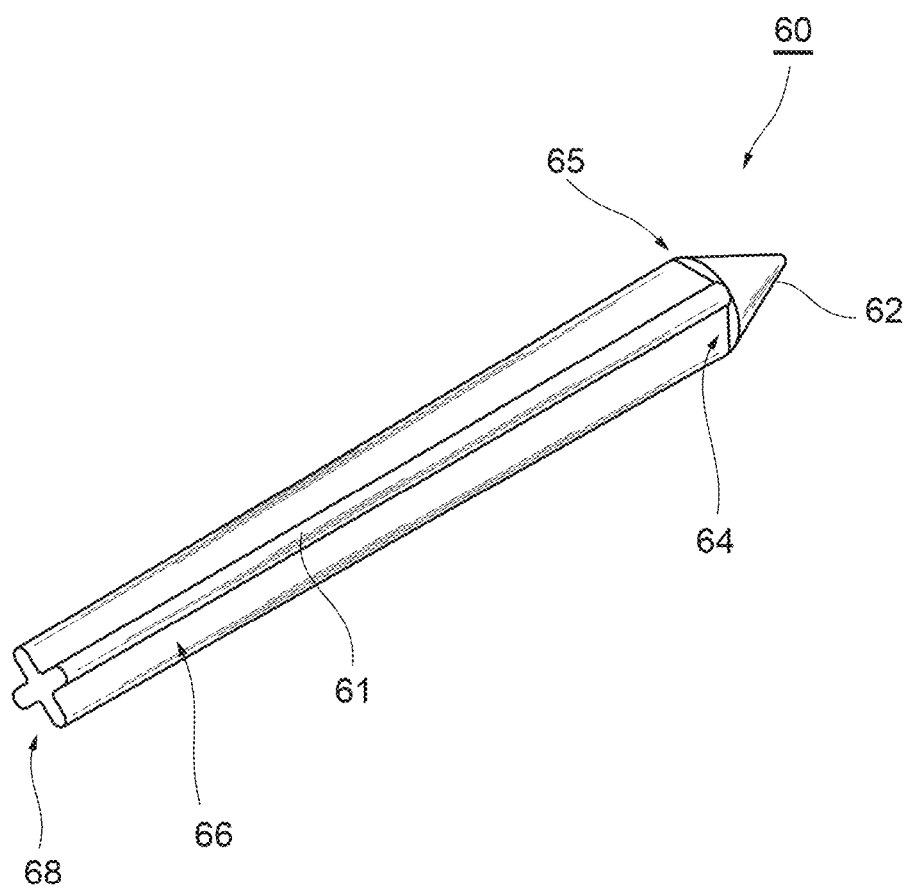
FIG. 11 is a perspective view, viewed from a base end portion side of the piercer.

A cap portion 64 is formed on a rear surface of the tip portion 62 of the piercer 60. The cap portion 64 is formed in such a manner that some of the air flowing into the filling space 22 through the hole formed in the sealing member 40 by the tip portion 62 is directed toward the outside in a radial direction. For example, the cap portion 64 of the intranasal delivery device for powdered medicine 10 according to the present embodiment is inclined as in an umbrella, so as to approach the tip portion from the outside to the inside in the radial direction (see FIGS. 11, 16, and the like). The cap portion 64 of the piercer 60 that is formed in the manner described above creates a downward airflow while guiding some of the air flowing into the filling space 22 toward the outside in the radial direction, and reduces the amount of powdered medicine M remaining in the filling space 22.

Groove portions 66 extending along a direction of movement of the piercer 60 (longitudinal direction) are formed in the shaft portion 61 of the piercer 60. When ejecting the powdered medicine M, the air inside the pump member 50 can flow into the filling space 22 through the groove portions 66 (see FIG. 16 and the like). The present embodiment adopts the piercer 60 in which the shaft portion 61 has a cross-shaped cross section where the groove portions 66 are formed on the four sides thereof (see FIGS. 10A to 10C and the like).

Figure 6A:
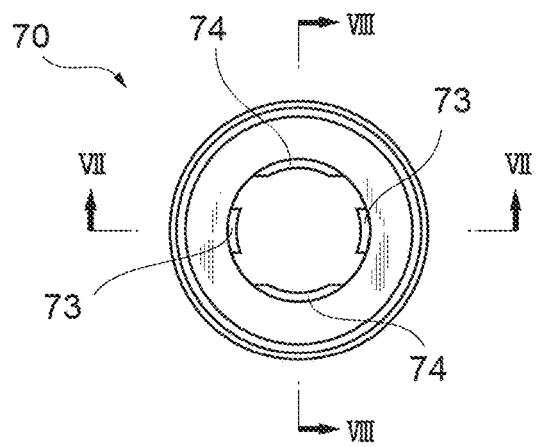
FIG. 6A shows a plan view of the holder.
Figure 6B:
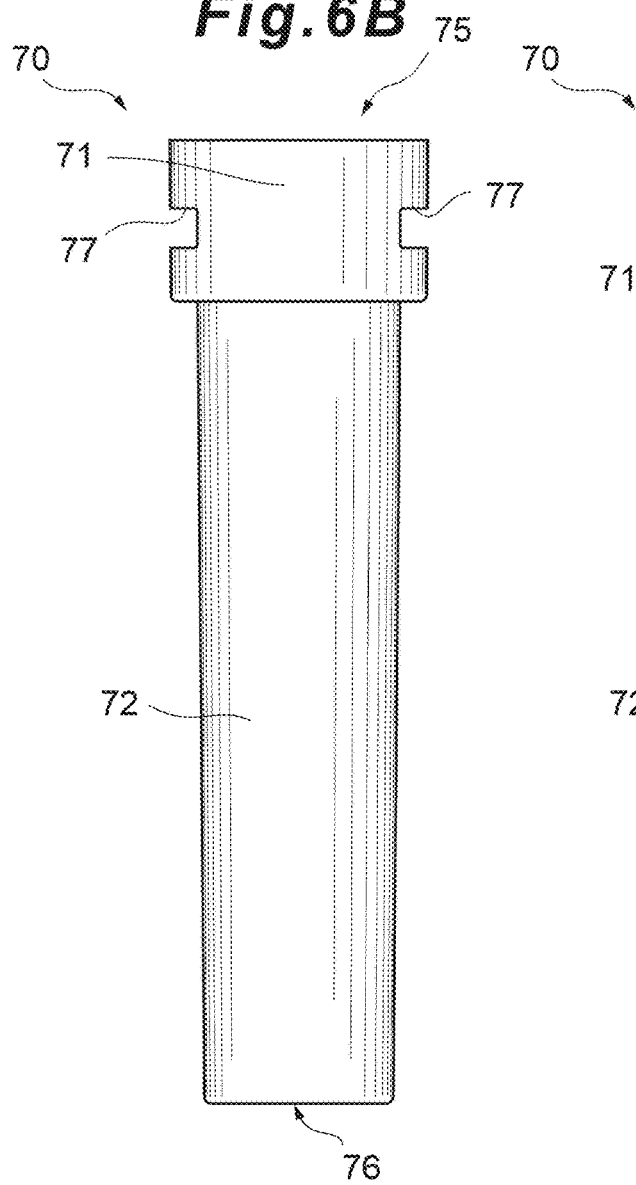
FIG. 6B shows a front view of the holder.
Figure 6C:
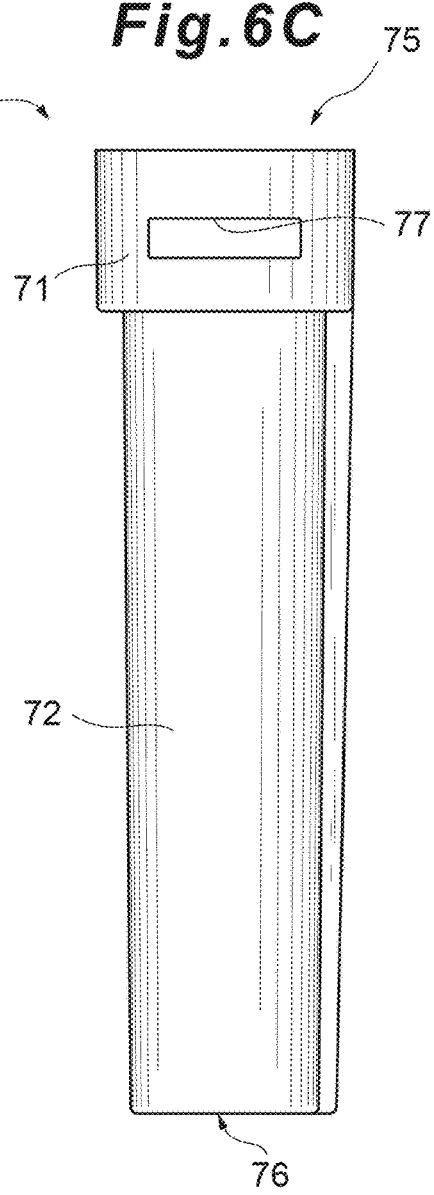
FIG. 6C shows a side view of the holder.
Figure 7:
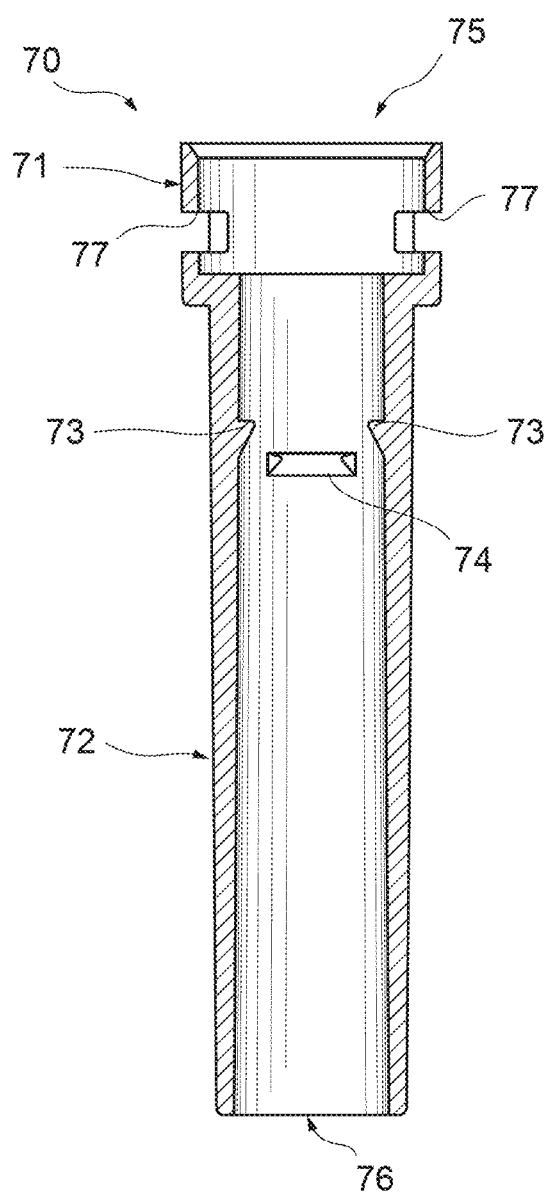
FIG. 7 is a vertical cross-sectional view of the holder, taken alone line VII-VII of FIG. 6A.
Figure 8:
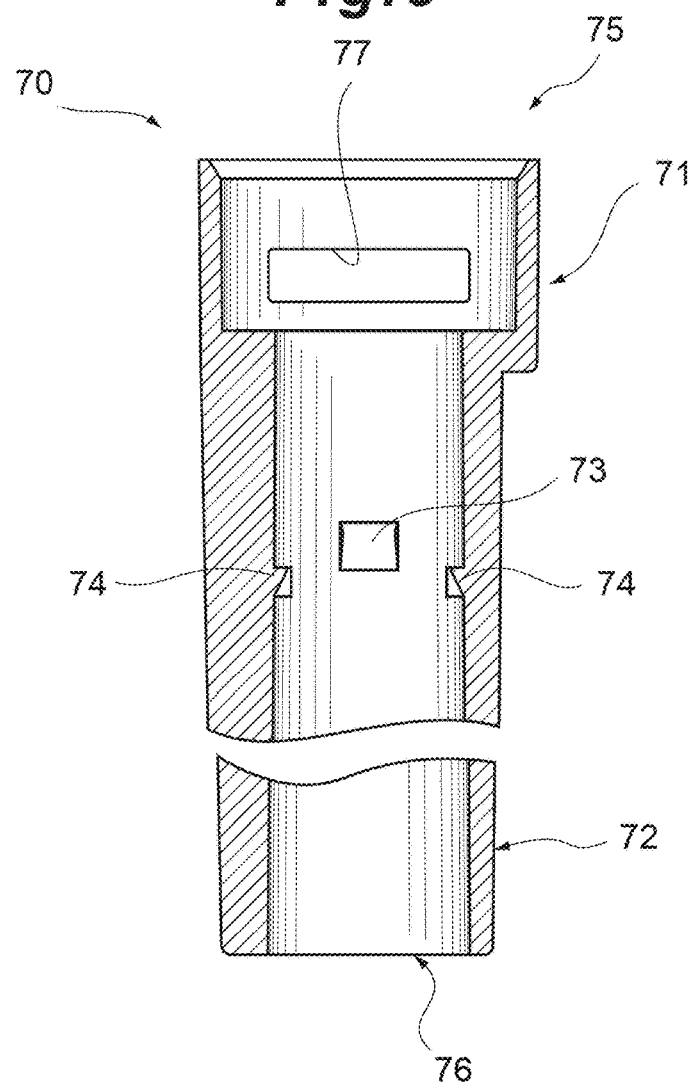
FIG. 8 is a vertical cross-sectional view of the holder, taken alone line VIII-VIII of FIG. 6A.
Figure 9:
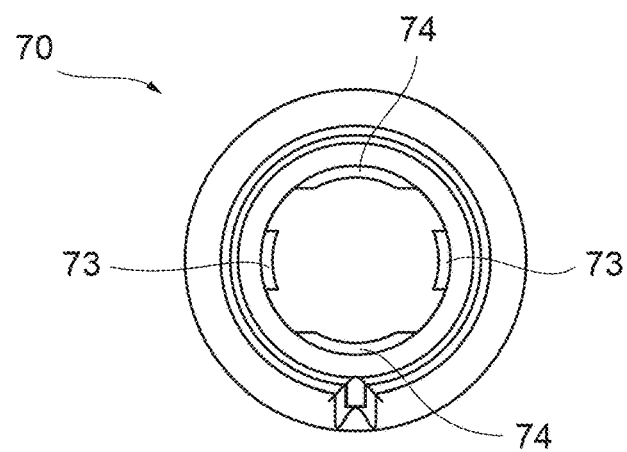
FIG. 9 is a bottom view of the holder.

The guide member (also referred to as "holder", hereinafter) 70 functions as a member that guides the piercer 60 while holding the piercer 60 and restricting the radial movement thereof when the piercer 60 moves. The holder 70 of the present embodiment includes a large diameter portion 71 and a sleeve-shaped small diameter portion 72 and is formed by a stepped cylindrical body in which the large diameter portion 71 is provided with a tip-side opening 75 and the small diameter portion 72 is provided with a base end-side opening 76 (see FIGS. 3A to 6C and the like). In addition, the large diameter portion 71 is provided at a position where a pair of slits 77 penetrating from an inner wall of the guide member 70 to an outer wall of the same face each other (see FIGS. 6A to 6C and the like).

As an example of fixing means for fixing the piercer 60 to a predetermined position, the inner wall of the holder 70 is provided with a piercer fixing upper click portion 73 and a piercer fixing lower click portion 74 (see FIGS. 5 to 13 and the like). The piercer fixing upper click portion 73 is formed by a pair of protrusions that is disposed so as to face the inner wall of the holder 70. The piercer fixing lower click portion 74 is formed by a pair of protrusions that is disposed so as to face a position at the base end side from the piercer fixing upper click portion 73 at the inner wall of the holder 70 (see FIG. 7 and the like). The distance (gap) between these opposing protrusions is slightly smaller than a maximum diameter of the tip portion 62 of the piercer 60, that is, a diameter of the edge portion 65 (see FIGS. 12, 13, and the like). Also, in the present embodiment, the protrusions (ribs) of the piercer fixing upper click portion 73 and the piercer fixing lower click portion 74 are arranged at 90 degree intervals in a circumferential direction (see FIG. 9 and the like) so that the circumferential positions of the protrusions are shifted from one another, and the protrusions can be molded with an injection molding machine.

Figure 12:
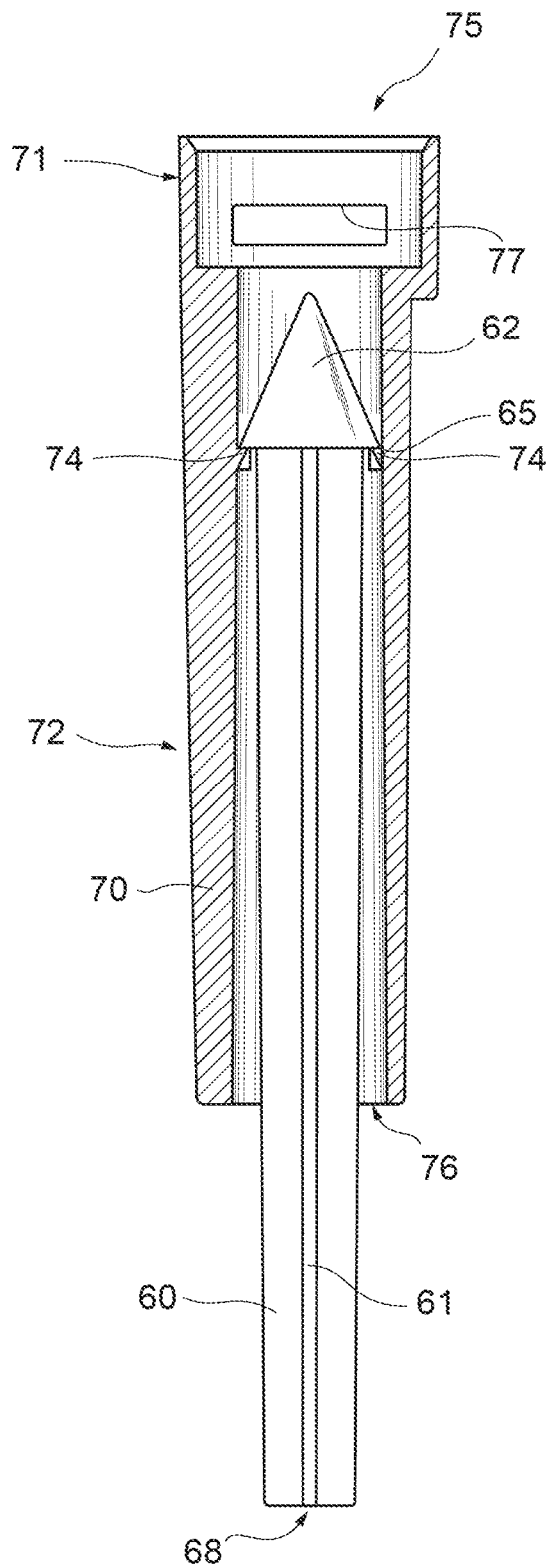
FIG. 12 is a vertical cross-sectional view of the piercer and the holder, taken along XII-XII of FIG. 5.
Figure 13:
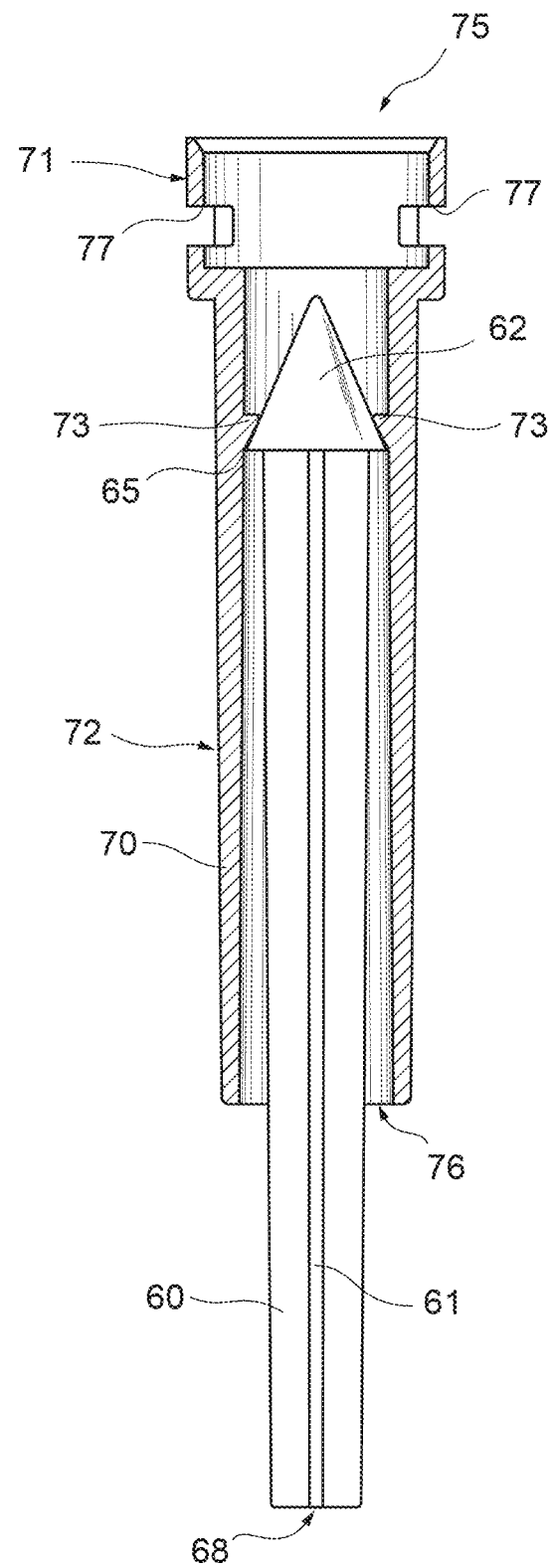
FIG. 13 is a vertical cross-sectional view of the piercer and the holder, taken along XIII-XIII of FIG. 5.

The piercer fixing upper click portion 73 and the piercer fixing lower click portion 74 each have an inclined surface in which the amount of protrusion thereof from the inner wall of the holder 70 increases from the base end side to the tip side of the piercer 60 (see FIGS. 12, 13, and the like). The piercer 60 is disposed in such a manner that the edge portion 65 is positioned between the piercer fixing upper click portion 73 and the piercer fixing lower click portion 74 in the axial direction. In a case where the piercer 60 is pushed toward the tip side, the edge portion 65 of the piercer 60 can move past the piercer fixing upper click portion 73 toward the tip side (see FIG. 13 and the like). On the other hand, even when the piercer 60 is pulled toward the base end side, the edge portion 65 of the piercer 60 cannot pass over the piercer fixing lower click portion 74 (see FIG. 12 and the like).

Furthermore, in the intranasal delivery device for powdered medicine 10 of the present embodiment, prior to the use thereof, the base end portion 68 of the piercer 60 and the bottom portion 52 of the pump member 50 are separated from each other, and a predetermined clearance C is formed therebetween (see FIG. 14 and the like). As will be described with reference to FIG. 17 and the like, the air pressure obtained when dispensing the powdered medicine M can be changed by appropriately changing the size of the clearance C.

<Operations of Intranasal Deliver Device for Powdered Medicine>

Operations of the intranasal delivery device for powdered medicine 10 that are performed when dispensing the powdered medicine M are described next (see FIGS. 14 to 17 and the like).

When using intranasal delivery device for powdered medicine 10, first the user takes out the intranasal delivery device for powdered medicine 10 from a box-shaped package, a blister package, or a pouch-like package (not shown), and breaks the tab 30 off the nozzle member 20 to open the ejection opening 26.

The user then hooks his/her index finger and middle finger onto the finger hook portions 54, places his/her thumb onto the bottom portion 52, pinches the pump member 50 with said fingers, and aims the ejection opening 26 of the nozzle member 20 toward nostrils. In this state, when the user pushes up the bottom portion 52 to press the pump member 50 (see FIG. 14(A) and the like), the intranasal delivery device for powdered medicine 10 moves as follows. Note that the force acting on the pump member 50 on the basis of the operation by the user (or stress generated on the pump member 50 itself) is called "pump pushing force" in the present specification and drawings (see FIG. 17).

The pump member 50 contracts by the clearance C, and the bottom portion 52 comes into abutment with the base end portion 68 of the piercer 60 (see FIG. 14(B)). After the operation of the pump member 50 is started, the piercer 60 is constantly held by the holder 70 and the sealing member 40 is not punctured until the bottom portion 52 comes into abutment with the base end portion 68 of the piercer 60. For this reason, the air inside the pump member 50 does not flow into the nozzle member 20. Therefore, the internal pressure of the pump member 50 increases by the distance of contraction of the pump member 50.

After the bottom portion 52 comes into abutment with the base end portion 68 of the piercer 60, the pump pushing force of the user is transmitted directly to the piercer 60 via the bottom portion 52. In a case where the user continues to push the bottom portion 52 so the pump pushing force exceeds a predetermined value, a force that separates the piercer 60 ("piercer separation force") acts, whereby the edge portion 65 of the piercer 60 passes over the piercer fixing upper click portion 73, enabling the piercer 60 to move with respect to the holder 70 (see (i) to (iii) of FIG. 17).

In a case where the piercer 60 is still continuously pushed after separating from the holder 70, the tip portion 62 comes into abutment with the sealing member 40, puncturing the sealing member 40 (see FIGS. 14(B) and 15(B)). This causes the air inside the pump member 50 to flow into the nozzle member 20. While the piercer 60 punctures the sealing member 40 (but when the tip portion 62 has not yet penetrated the sealing member 40), the pump pushing force gradually increases due to the resistance received from the sealing member 40, the internal pressure of the pump member 50, and the reaction force of the bellows portion 51 (see (iv) of FIG. 17). When the pump pushing force reaches the peak thereof (see (v) of FIG. 17) immediately before the tip portion 62 of the piercer penetrates the sealing member 40, and when the tip portion 62 penetrates the sealing member 40, the pump pushing force drops rapidly (see (vi) of FIG. 17). As a result of the tip portion 62 of the piercer 60 penetrating the sealing member 40, the air flows into the nozzle member 20 at once, ejecting the powdered medicine M from the ejection opening 26 (see FIG. 15(C)).

Figure 16:
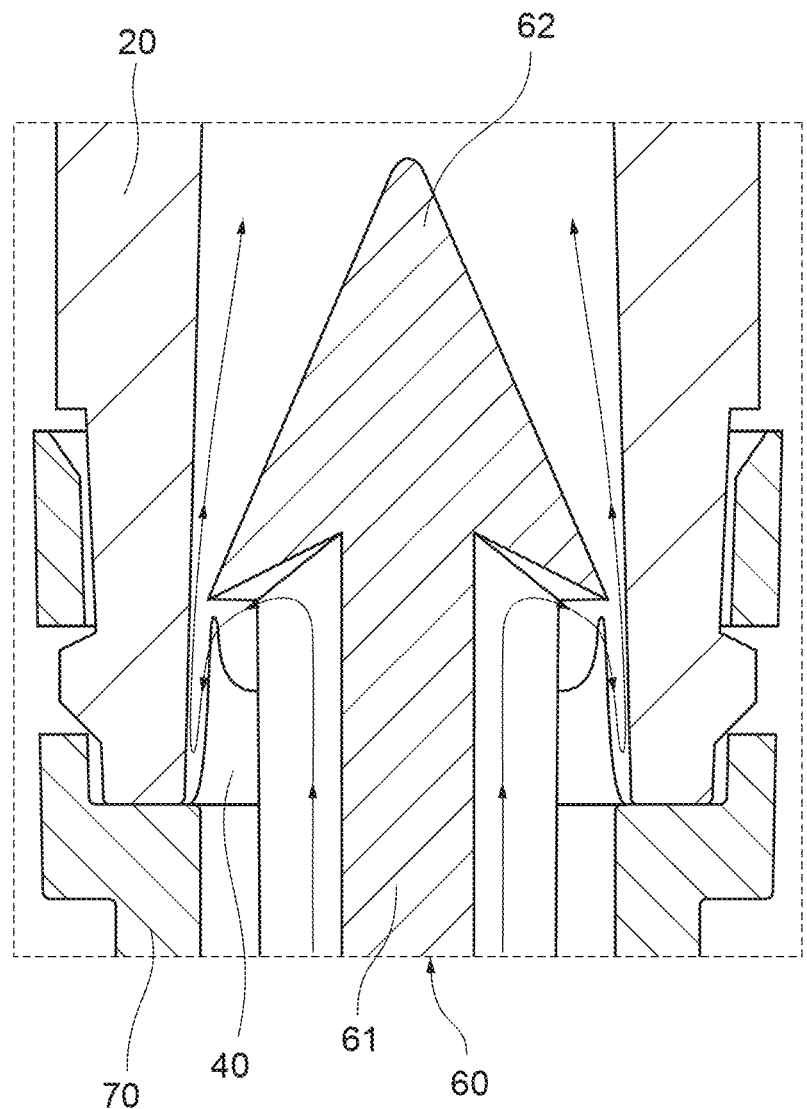
FIG. 16 is a partial vertical cross-sectional view for explaining a flow of air around a tip portion of the piercer that is obtained when dispensing the powdered medicine M.

Movements of the air and the powdered medicine M at the time of ejection are now described (see FIG. 16 and the like). The air inside the pump member 50 flows through the space between the groove portion 66 of the piercer 60 and the holder 70, passes through the hole formed in the sealing member 40, and flows into the filling space 22 in the nozzle member 20. At least some of the air that has flowed into the nozzle member 20 flows so as to generate a downward airflow by means of the cap portion 64 of the piercer 60 while moving radially outward, and thereafter flows toward the ejection opening 26 (see FIG. 16). By causing the air to flow in the filling space 22 within the nozzle member 20 in this manner, the powdered medicine M, which tends to remain in the vicinity of an edge of the sealing member 40, is also ejected, so that the amount of powdered medicine M remaining in the filling space 22 can be reduced.

Figure 17:
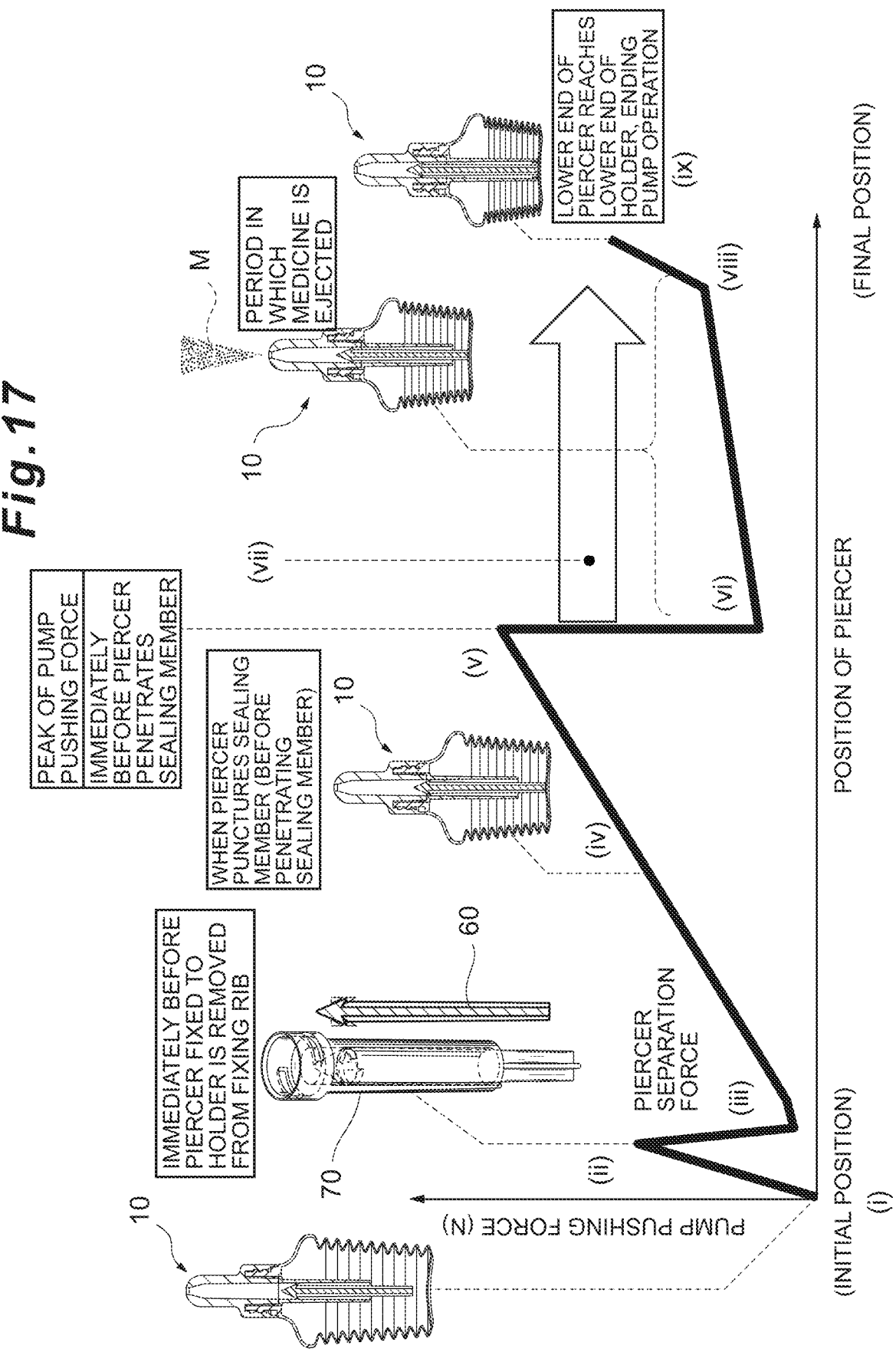
FIG. 17 is a graph showing the relationship between an axial position of the piercer and a pump pushing force from the start to the end of a pump operation performed to dispense the powdered medicine M.
Figure 18:
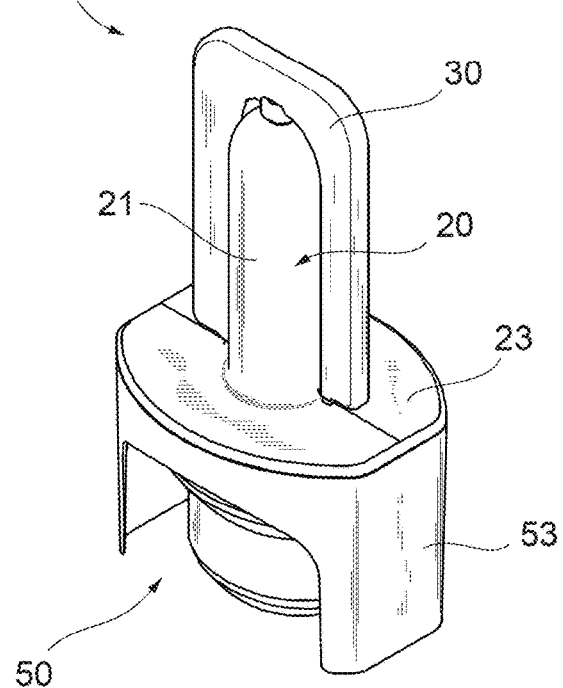
FIG. 18 is a perspective view of the intranasal delivery device for powdered medicine (medicine dispensing device) according to a second embodiment of the present invention.
Figure 19:
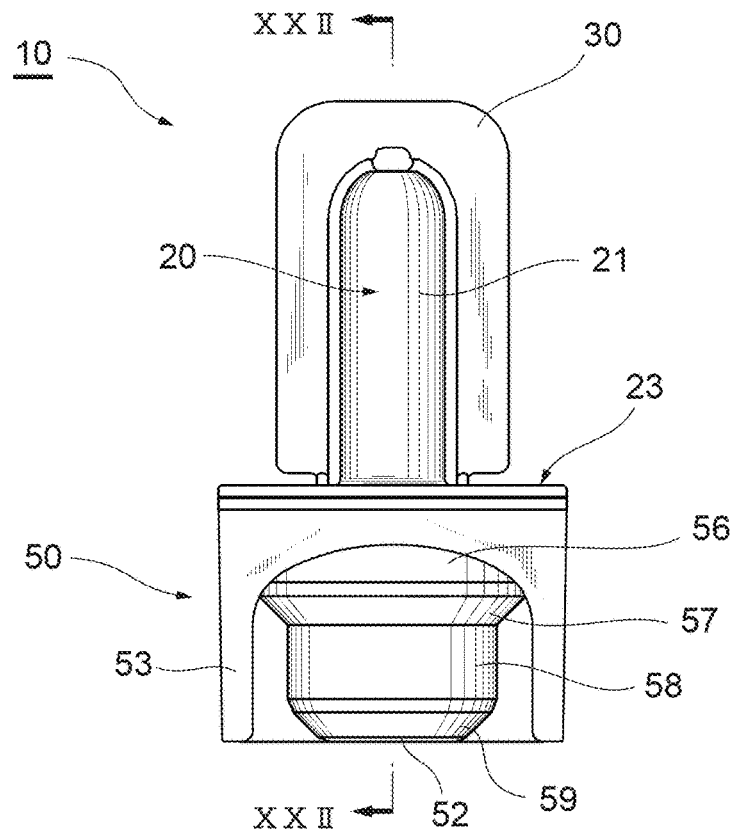
FIG. 19 is a front view of the intranasal delivery device for powdered medicine.
Figure 20:
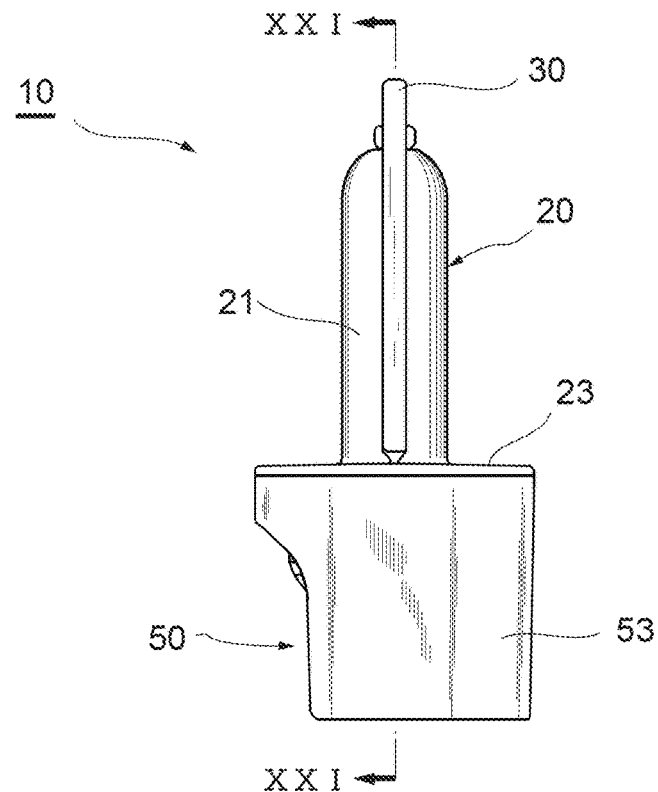
FIG. 20 is a right side view of the intranasal delivery device for powdered medicine.

In the intranasal delivery device for powdered medicine 10 of the present embodiment, the pump member 50 and the piercer 60 are pushed directly to a final position (in the present embodiment, the position where the bottom portion 52 comes into abutment with the base end-side opening 76 of the holder 70 and stops moving) by the momentum of the pump pushing force that has reached the peak (see FIGS. 14(D), 15(D), and 17). Generally, the level of the pump pushing force and how the pump pushing force changes can differ due to differences in various factors such as the user and usage conditions. However, according to the intranasal delivery device for powdered medicine 10 of the present embodiment that realizes the operations described above, since the variation in the pushing force obtained when the tip portion 62 of the piercer 60 penetrates the sealing member 40 is reduced, and as a result, the variation in how the powdered medicine M is ejected is suppressed (see (vi) to (viii) of FIG. 17).

Subsequent to the foregoing operation described above, the operation is discontinued when the pump member 50 and the piercer 60 reach the final position (in the case of the present embodiment, the position where the bottom portion 52 comes into abutment with the base end-side opening 76 of the holder 70 and stops moving), ending the pump operation (see FIG. 14(D), and (ix) of FIG. 17)

<Characteristics of Intranasal Delivery Device for Powdered Medicine>

Characteristics of the above-mentioned intranasal delivery device for powdered medicine 10 of the present embodiment are described hereinafter.

While the conventional devices in which the nozzle is reused has hygiene issues (cleaning is required when the nozzle becomes soiled from nasal discharge or the like), in the present embodiment, as the intranasal delivery device for powdered medicine 10, a single-use device with a nozzle is employed; problems related to reusing of the device can be avoided.

While the conventional devices in which the nozzle is reused have the problem that the medicine remaining in the nozzle become decomposed or denatured, and consequently the decomposed products or denatured products are administered (requiring cleaning of the nozzle), the intranasal deliver device for powdered medicine 10 of the present embodiment is favorably configured as a single-use device by making the device itself into a cartridge; such a problem related to reusing of the device can be avoided.

Regarding medicines with low storage stability, the conventional devices faced the problem of ensuring storage stability in the medicine container (unsuitable for medicines that are easily decomposed or denatured by humidity, oxygen, etc.). On the other hand, in the intranasal deliver device for powdered medicine 10 according to the present embodiment, the filling space 22 in the nozzle member 20 functions as a sealing container by sealing the filling space 22 with the tab 30 and the sealing member 40, so that such a problem does not occur. The intranasal delivery device for powdered medicine 10 having such a structure can easily be applied to the powdered medicine M that is sensitive to oxygen and humidity.

While the conventional devices faced the problem where the dose is not stable because the medicine drops into the pump or the device and thereby the injection amount is reduced or because the dropped medicine is additionally administered at the next administration, in the intranasal delivery device for powdered medicine 10 of the present embodiment, the injection begins almost at the same time as when the sealing member 40 is punctured; the foregoing problem can be avoided as well.

In the conventional device, in order to open an air vent in a stopper of the medicine container, the air vent is provided by piercing the capsule with a needle or the like and then pulling out the needle or the like from the capsule, which results in easy breakage of the container and consequently results in administering the broken pieces of the container into the body along with the medicine. On the other hand, according to the intranasal delivery device for powdered medicine 10 of the present embodiment, the sealing member 40 is punctured with the pointy tip of the piercer 60, and then, without pulling the pointy tip of the piercer 60 out of the sealing member 40, the air vent can be formed; the foregoing problem can be avoided as well.

While the conventional device faced the problem where how the medicine is ejected varies depending on how the pump is pushed, in the intranasal delivery device for powdered medicine 10 of the present embodiment, even when different users use the intranasal delivery device for powdered medicine 10, the pump operation performed until shortly before the tip portion 62 of the piercer 60 penetrates the sealing member 40 fills the pump with some of the ejection air with a constant amount and pressure, and the following pump operation causes the tip portion 62 of the piercer 60 to penetrate the sealing member 40, and at the same time the constant amount of air filling the pump flows into the medicine container (the filling space 22 of the nozzle member 20 that functions as the medicine container) and injects the powdered medicine M; the foregoing a problem can be avoided. In addition, in the intranasal delivery device for powdered medicine 10 of the present embodiment, since the pushing force of the tip portion 62 of the piercer 60 penetrating the sealing member 40 is set at the maximum pushing force of the pump operation, the momentum of the pump operation released from the maximum pushing force can bring the rest of the pump operation to completion. Therefore, since a constant amount of air flows into the medicine container to inject the powdered medicine M, the foregoing problem can be avoided.

In the conventional device, the preparation before administration such as attaching the capsule or cartridge is often complicated. The intranasal delivery device for powdered medicine 10 of the present embodiment, on the other hand, is a single-use device in which the nozzle member 20, the pump member 50, and the like are integrated from the beginning, and therefore does not require preparations such as assembling, tearing off a seal, or the like.

Although the foregoing embodiment is an example of a preferred embodiment of the present invention, the present invention is not limited thereto, and various modifications can be made without departing from the gist of the present invention. For example, although not particularly described in the foregoing embodiment, the intranasal delivery device for powdered medicine 10 may further include a return motion prevention member that prevents the pump member 50 from returning to the original state thereof after contracting. In the intranasal delivery device for powdered medicine 10 provided with the return motion prevention member, the ejected powdered medicine M is prevented from being drawn into the ejection opening 26. Specific configurations of the return motion prevention member are not particularly limited. For example, a member that is a cylindrical or ring-shaped protrusion formed at the center on the inside of the bottom portion 52 of the pump member 50 and reaches the inside (or may be the outside) of the base end-side opening 76 of the holder 70 to prevent the contracted pump member 50 from returning to the original state thereof by keeping the contracted pump member 50 as is, can be used as the return motion prevention member (shown by reference numeral 80 in FIG. 14(D)).

Although the intranasal delivery device for powdered medicine 10 is suitable as a device for administering a nasal medicine, the use thereof is not particularly limited thereto. For example, currently, nasal administration is mainly for topical treatment for treating mainly sinus infection. However, recently, there exist a large number of commercialized nasal medicines that aim to absorb, through the nasal mucosa, medications that are expected to have systemic effects, such as medications for relieving migraine and cancer pain, and the use of the intranasal delivery device for powdered medicine 10 includes such application. Furthermore, studies have been conducted to transfer a medication from the olfactory region inside the nasal cavity to the brain, and the use of the intranasal delivery device for powdered medicine 10 also includes delivering the nasal medicine to the olfactory region inside the nasal cavity. In addition, in the development of medical products, the development of biomedicines that require strict dose control and strict storage management has been accelerating, and the need for nasal application of these medicines has been increasing. The use of the intranasal delivery device for powdered medicine 10 also includes such application.

Specific examples other than the administration of a nasal medicine include the following.

Cartridges that are used to store bioactive substances such as low-molecular compounds, peptide drugs, vaccines, nucleic acids, proteins, and antibodies.

Intranasal delivery devices for powdered medicines (intranasal powdered medicine dispensing devices) that are used to administer bioactive substances such as low-molecular compounds, peptide drugs, vaccines, nucleic acids, and proteins.

Intranasal delivery devices for powdered medicines (intranasal powdered medicine dispensing devices) that are used to achieve topical action on sinus infection, paranasal sinusitis, and the like.

Intranasal delivery devices for powdered medicines (intranasal powdered medicine dispensing devices) that are used to absorb, through the nasal mucosa, medications that are expected to have systemic effects.

Intranasal delivery devices for powdered medicines (intranasal powdered medicine dispensing devices) used for mucosal immune effect.

Intranasal delivery devices for powdered medicines (intranasal powdered medicine dispensing devices) that are used to transfer a medication from the olfactory region inside the nasal cavity to the brain.

Since the intranasal delivery device for powdered medicine 10 described above includes the nozzle member 20 that has a filling space to be filled with a predetermined dose of a powdered medicine, the improvement in uniformity of each dose can easily be realized by, preferably, filling the filling space with a single dose of the medicine. In addition, the present invention can specialize in implementation in which a single dose of a medicine is used up at once, in which case the improvement in portability can be realized easily by reducing the size and weight of the device. In other words, the nozzle member 20 can be caused to function as a container for a powdered medicine (with a single dose), achieving a structure that can easily realize the improvement of dose uniformity and portability.

Furthermore, adopting the form in which a single dose of a medicine is used up at once can overcome the hygiene problems due to the multiple use of the nozzle, such as the need to clean the nozzle when the nozzle becomes soiled from nasal discharge or the like after repetitive use of the nozzle, and administration of a denatured or decomposed medicine remaining in the nozzle into the body.

The intranasal delivery device for powdered medicine 10 described above can particularly favorably be applied to medicines that easily take up moisture or become oxidized, by adopting a configuration in which a sealing space is formed in the nozzle member 20 by sealing the opening 24 of the nozzle member 20 with the sealing member 40, and the piercer 60 forms a hole by puncturing in the sealing member 40 as the powdered medicine is ejected.

In addition, in the intranasal delivery device for powdered medicine 10 described above, preferably, by filling the nozzle member with a single dose of the medicine in advance and sealing the nozzle member until use, the medicine dispensing device can not only solve problems that may occur in association with medical efficacy and toxicity related to storage stability in the medicine container (problem that the medicine dispensing device is not suitable for medicines that are easily decomposed or denatured due to humidity, oxygen, etc.), but also improve the preservation of the medicine.

In the intranasal delivery device for powdered medicine 10 described above, it is preferred that the positional relationship between the bottom portion 52 of the pump member 50 and the piercer 60 and the characteristics of the generated air be changed appropriately in accordance with various characteristics such as the characteristics of the sealing member 40 when being punctured and how compressed air flows, or in order to adjust these characteristics. For example, in the intranasal delivery device for powdered medicine 10 described above, the size of a clearance C1 has a significant impact in the first stage of generating the compressed air during the pump operation, and the size of a clearance C2 has a significant impact in the second stage of generating the compressed air during the pump operation (see FIG. 14(A)). With this point in mind, for example, in a case where the compressed air is required as the characteristics of the air generated when the powdered medicine M is injected, the pressure and amount of the compressed air to be generated can be controlled by adjusting strokes in the clearance C1 and/or the clearance C2 and a pump internal capacity corresponding to each stroke. Furthermore, in a case where the compressed air is not required as the characteristics of the air generated at the time of the injection, the air can be caused to flow into the nozzle member 20 almost at the same time as the operation of the pump member 50 by not providing the clearance C1 and/or the clearance C2 (see FIG. 14).

Second Embodiment

The medicine dispensing device (also called "intranasal delivery device for powdered medicine", hereinafter) 10 according to a second embodiment is now described hereinafter (see FIGS. 18 to 29).

The intranasal delivery device for powdered medicine 10 is a single-use device for dispensing a predetermined dose of a powdered medicine into a nasal cavity of a patient. The intranasal delivery device for powdered medicine 10 of the present embodiment includes the nozzle member 20, the tab 30, the sealing member 40, the pump member 50, and the piercer 60 (see FIG. 23 and the like).

Figure 24:
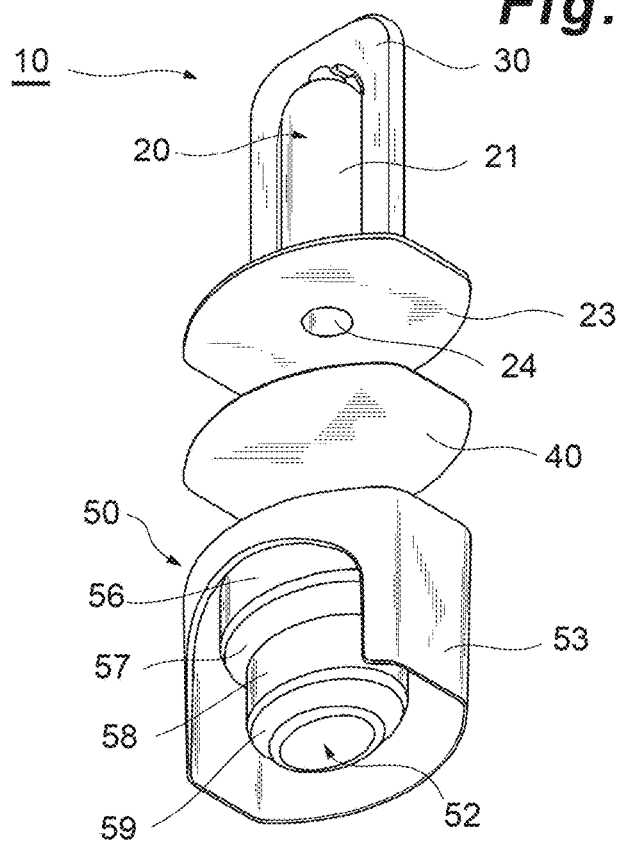
FIG. 24 is an exploded perspective view in which the intranasal delivery device for powdered medicine is viewed from obliquely below.
Figure 25:
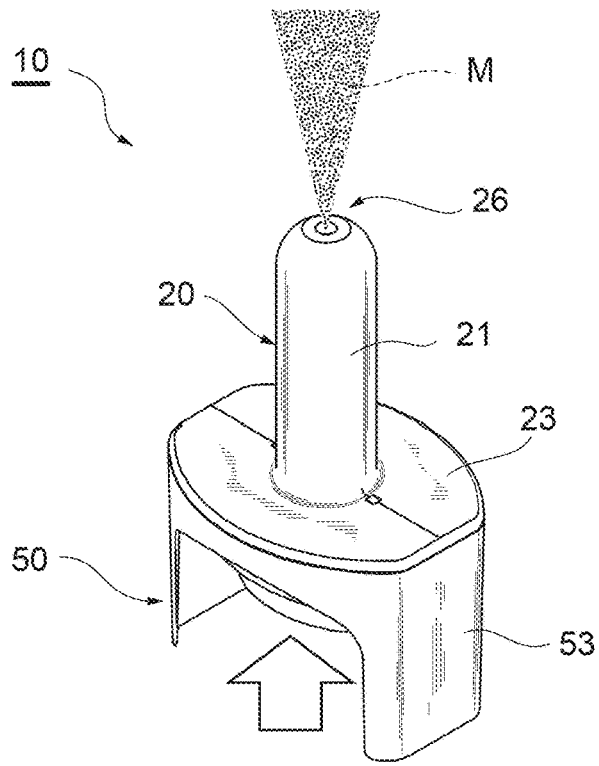
FIG. 25 is a perspective view of the intranasal delivery device for powdered medicine in use.

The nozzle member 20 includes a cylindrical portion 21 that is provided with roundness at a tip thereof so as to facilitate the administration of a powdered medicine into a nasal cavity of a patient, and a flange portion 23 formed on the base end side of the cylindrical portion 21 (see FIG. 24 and the like). The filling space 22 that is filled with the medicine is formed inside the cylindrical portion 21 (see FIGS. 21, 22, and the like). The ejection opening 26 for ejecting the powdered medicine M is provided at the center of the tip of the cylindrical portion 21 of the nozzle member 20 (see FIGS. 28, 29, and the like). The opening 24 through which the filling space 22 can be filled with the powdered medicine M is formed at the center on the base end side of the cylindrical portion 21 (the side of the cylindrical portion 21 attached to the pump member 50 side) (see FIG. 24 and the like).

Figure 26:
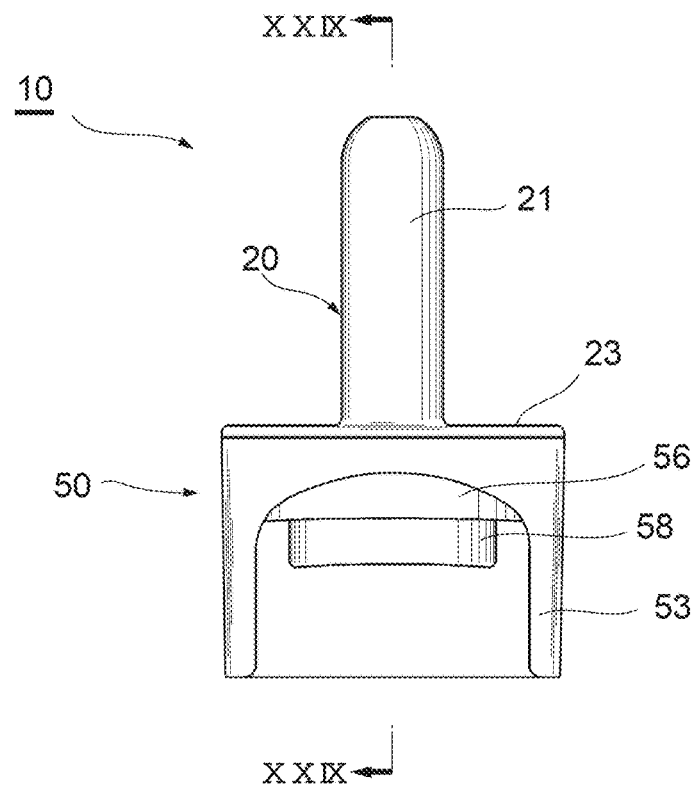
FIG. 26 is a front view of the intranasal delivery device for powdered medicine after use.
Figure 27:
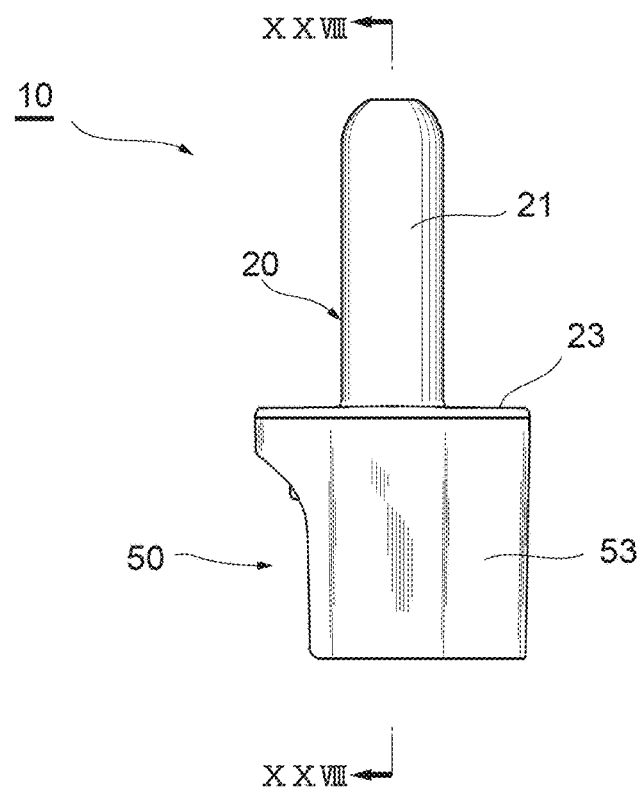
FIG. 27 is a right side view of the intranasal delivery device for powdered medicine after use.
Figure 28:
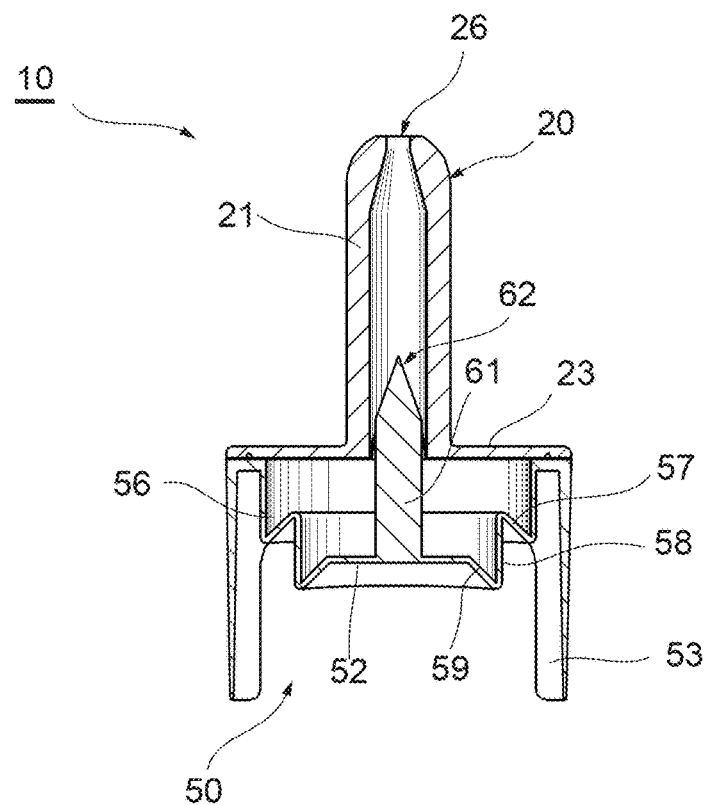
FIG. 28 is a cross-sectional view of the intranasal delivery device for powdered medicine after use, taken along line XXVIII-XXVIII of FIG. 27.

The flange portion 23 is shaped to allow the user such as a patient to put his/her fingers (especially an index finger and a middle finger) easily, and functions as the finger hook portion 54 of the intranasal delivery device for powdered medicine 10 described in the foregoing embodiment (see FIG. 26 and the like). By hooking the index finger and the middle finger on the respective shoulder portions of the flange portion 23, the user can easily push the bottom portion 52 with his/her thumb to cause the pump member 50 to contract.

Figure 22:
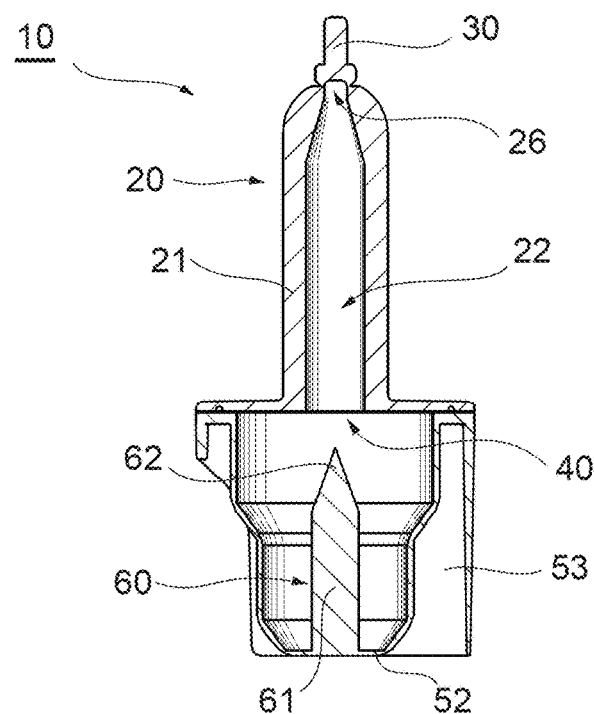
FIG. 22 is a cross-sectional view of the intranasal delivery device for powdered medicine, taken along line XXII-XXII of FIG. 19.
Figure 23:
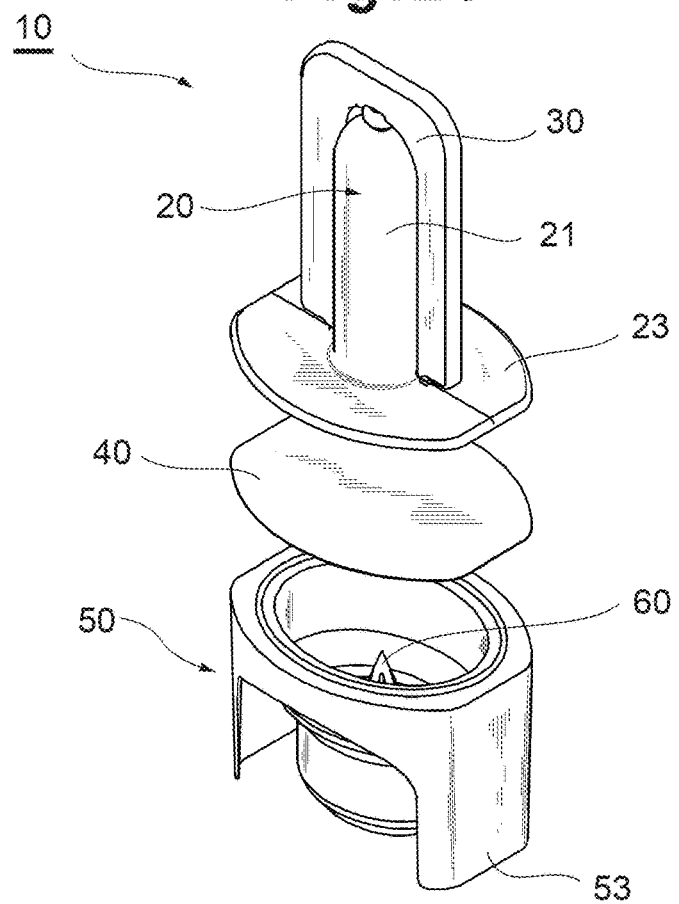
FIG. 23 is an exploded perspective view in which the intranasal delivery device for powdered medicine is viewed from obliquely above.

The sealing member 40 is a member for sealing the opening 24 of the filling space 22 of the nozzle member 20 (see FIGS. 22, 24, and the like). It is preferred that a moisture-proof film sheet or the like that not only seals the filling space 22 to prevent the powdered medicine M from being deteriorated by air or moisture but also can easily be punctured with the piercer 60 at the time of use, be used as the sealing member 40. The present embodiment adopts the sealing member 40 that maintains airtightness without tearing or peeling even when the internal pressure of the pump member 50 rises to a predetermined level. The sealing member 40 of the present embodiment is formed in accordance with the shape and size of a bottom surface of the flange portion 23 or an upper surface of the pump member 50, and is attached so as to be interposed between the flange portion 23 and the pump member 50 (see FIGS. 19, 20, and the like).

The pump member 50 is a member that feeds air to eject the powdered medicine M from the ejection opening 26 of the nozzle member 20 when the intranasal delivery device for powdered medicine 10 is being used. In the present embodiment, the pump member 50 that is configured to collapse when the user pushes the bottom portion 52 with his/her finger is adopted (see FIG. 25 and the like). Specific shapes or structures of the pump member 50 are not particularly limited; it is preferred that the pump member 50 collapse evenly and neatly without tilting on one side, regardless of differences in finger size, pushing force, pushing direction, etc. of each user. Moreover, the powdered medicine M can be ejected more efficiently as long the air inside the pump member 50 can be fed as completely as possible.

Figure 21:
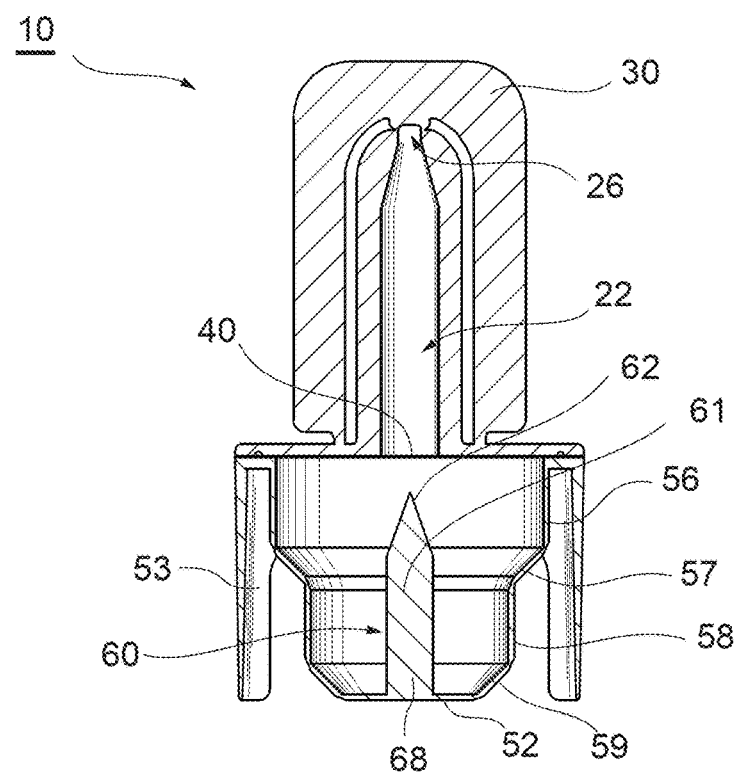
FIG. 21 is a cross-sectional view of the intranasal delivery device for powdered medicine, taken along line XXI-XXI of FIG. 20.

For example, the pump member 50 according to the present embodiment is configured to include a cylindrical, large diameter portion 56, a first tapered portion 57 that is continuous from the large diameter portion 56 so as to taper down, a cylindrical, small diameter portion 58 continuing to the first tapered portion 57, and a second tapered portion 59 formed between the small diameter portion 58 and the substantially disc-shaped bottom portion 52 (see FIG. 21 and the like). In this pump member 50, pushing the bottom portion 52 deforms the first tapered portion 57 and the second tapered portion in such a manner that the first tapered portion 57 and the second tapered portion are folded back toward the base end side, embedding the bottom portion 52 into the small diameter portion 58 and a part of the small diameter portion 58 into the large diameter portion 56 (see FIGS. 25 to 29). After the bottom portion 52 is embedded into the small diameter portion 58 and a part of the small diameter portion 58 is embedded into the large diameter portion 56, the pump member 50 cannot easily return to the original state thereof since the pump member 50 is made of a plastic material.

The pump member 50 of the present embodiment further includes a pump malfunction prevention cover 53. The pump malfunction prevention cover 53 is provided in order to prevent the pump member 50 from collapsing and the powdered medicine M from being ejected before usage, and is composed of a wall-like member that covers three sides of the periphery such as the bottom portion 52, the small diameter portion 58, and the like (see FIG. 24 and the like). The pump malfunction prevention cover 53 is not provided on the front side (or the rear side) of the pump member 50 so that the user can push the bottom portion 52 with his/her finger (mainly his/her thumb) (see FIGS. 19, 27, and the like).

Figure 29:
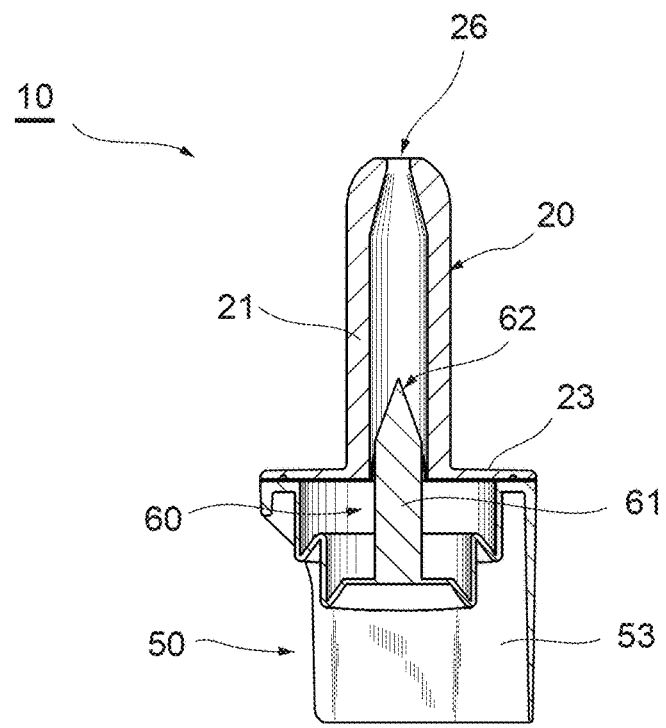
FIG. 29 is a cross-sectional view of the intranasal delivery device for powdered medicine after use, taken along XXIX-XXIX of FIG. 26.

The piercer 60 is a member that moves as the pump member 50 contracts, and forms a hole by puncturing in the sealing member 40 while moving, to release the sealed state (see FIG. 29 and the like). The piercer 60 of the present embodiment includes the shaft portion 61, the tip portion 62 facing the nozzle member 20 side, and the base end portion 68 facing the bottom portion 52 of the pump member 50. The tip portion 62 has a shape that allows easy formation of a hole by puncturing in the sealing member 40, such as a conical shape that tapers toward the tip (see FIG. 21 and the like).

In the pump member 50 described above, for example, a part of the piercer 60 is molded by means of injection molding, and outer portions thereof (the bottom portion 52, the second tapered portion 59, the small diameter portion 58, the first tapered portion 57, the large diameter portion 56, and the pump malfunction prevention cover 53, which are parts other than the piercer 60 in case of the pump member of the present embodiment) can be manufactured by integral molding by means of blow molding, injection molding, or vacuum molding. Note that, as described in the present embodiment, the pump member 50 can be configured so as to be easily removed from the forming die by, for example, forming the pump malfunction prevention cover 53 in such a manner as to become thinner from the tip end side toward the base end side (see FIG. 21 and the like) or in such a manner that the part from the large diameter portion 56 to the bottom portion 52 gradually tapers down.

The tab 30 is a member (closing member) for closing the ejection opening 26 of the nozzle member 20. The tab 30 of the present embodiment is a substantially U-shaped member that is welded to the nozzle member 20 at a total of three locations, i.e., the ejection opening 26 and two locations of the flange portion 23 (see FIG. 21 and the like). At the time of use, the ejection opening 26 opens when the user removes the tab 30 by twisting the tab 30 (see FIG. 26 and the like).

Third Embodiment

Figure 30:
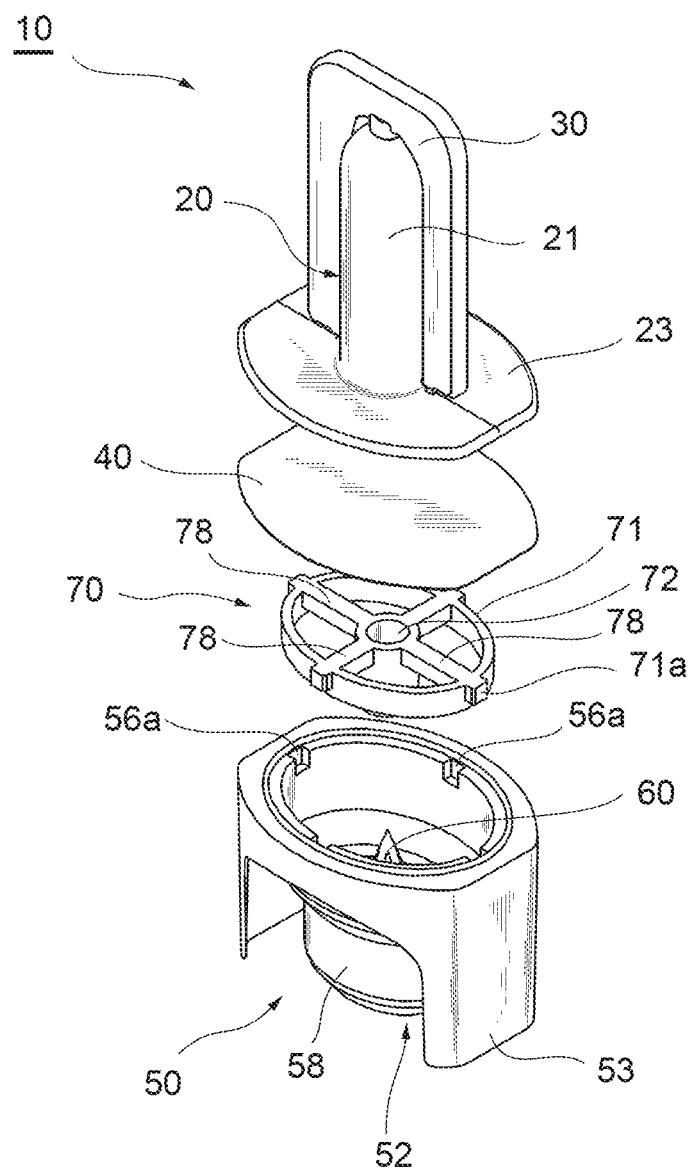
FIG. 30 is an exploded perspective view of the intranasal delivery device for powdered medicine (medicine dispensing device) according to a third embodiment of the present invention, the device further including a guide member.
Figure 31:
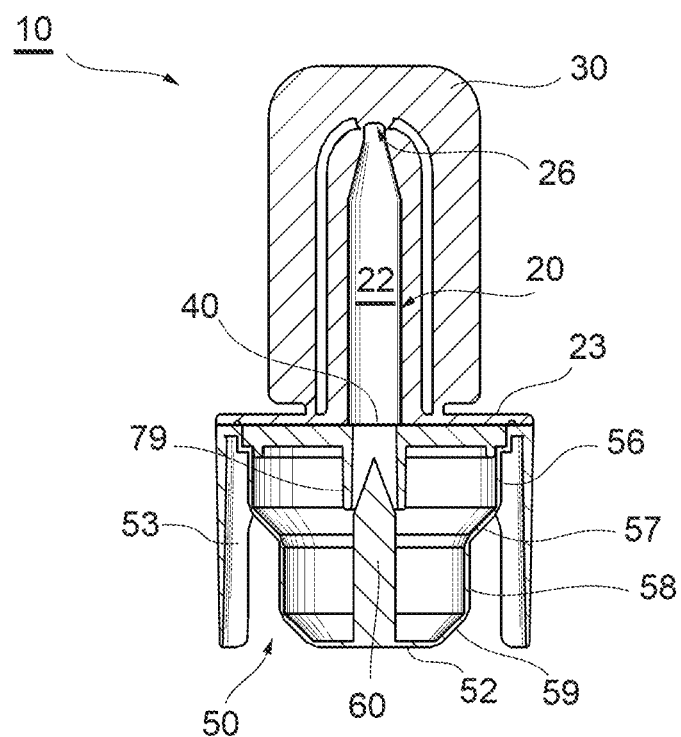
FIG. 31 is a vertical cross-sectional view of the intranasal delivery device for powdered medicine shown in FIG. 30.

The medicine dispensing device (also called "intranasal delivery device for powdered medicine") 10 according to a third embodiment is now described hereinafter (see FIGS. 30 and 31).

The intranasal delivery device for powdered medicine 10 of the present embodiment has a structure in which the guide member 70 is added to the intranasal delivery device for powdered medicine 10 of the second embodiment.

The guide member 70 is a member for securely piercing/puncturing the vicinity of the opening 24 of the sealing member 40 using the piercer 60. The guide member 70 of the present embodiment has a shape in which an annular large diameter portion 71 and an annular small diameter portion 72 are connected by a plurality of (four, for example) spoke portions 78 extending radially (see FIG. 30). The large diameter portion 71 is formed so as to much an inner diameter of the large diameter portion 56 of the pump member 50. The small diameter portion 72 restricts the piercer 60 from moving in a lateral direction (radial direction). A sleeve 79 extending toward the base end up to a position that overlaps with at least a part of the piercer 60 may be formed on the small diameter portion 72 (see FIG. 31). A small protrusion 71a may be provided around the large diameter portion 71, and a recessed portion 56a into which the small protrusion 71a is fitted may be provided on the inner peripheral side of the large diameter portion 56 of the pump member 50 (see FIG. 30).

Fourth Embodiment

In the intranasal delivery device for powdered medicine 10 according to the third embodiment, the groove portions 66 may be formed in the piercer 60. Such piercer 60 is described hereinafter as a fourth embodiment (see FIGS. 32 to 35).

Figure 32A:
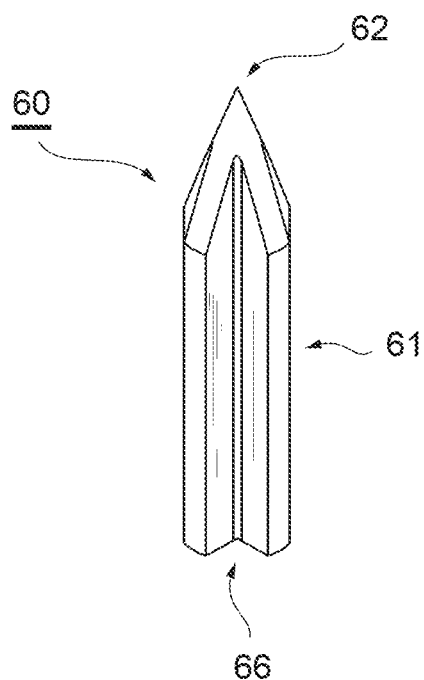
FIG. 32A shows a perspective view in which a piercer of the intranasal delivery device for powdered medicine (medicine dispensing device) according to a fourth embodiment of the present invention is viewed from obliquely above.
Figure 32B:
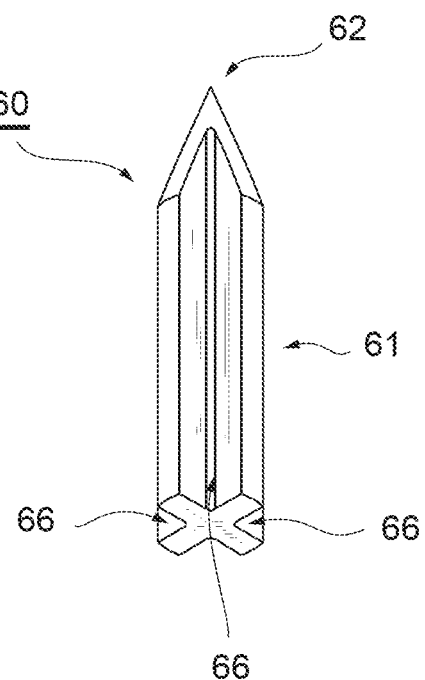
FIG. 32B shows a perspective view in which the piercer is viewed from obliquely below.
Figure 33:
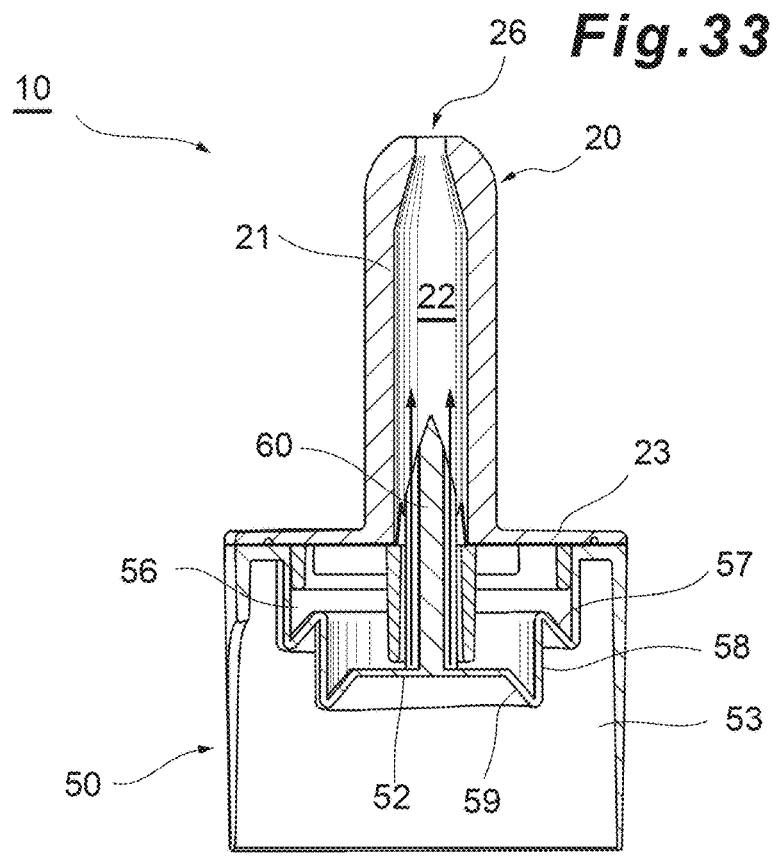
FIG. 33 is a vertical cross-sectional view for explaining a flow of air around the piercer that is obtained immediately after a hole is formed by puncturing in the sealing member with the piercer shown in FIGS. 32A and 32B.

The groove portions 66 extending along the direction of movement of the piercer 60 (longitudinal direction) may be formed in the shaft portion 61 of the piercer 60 (see FIGS. 32A and 32B). When the powdered medicine M is ejected, the air inside the pump member 50 can flow into the filling space 22 through the groove portions 66 (see FIG. 33). The present embodiment adopts the piercer 60 in which the shaft portion 61 has a cross-shaped cross section where the groove portions 66 are formed on the four sides thereof (see FIGS. 32 and 33).

Figure 34A:
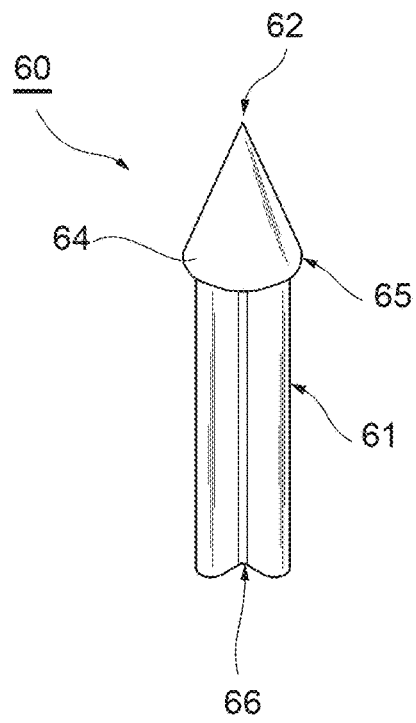
FIG. 34A shows a perspective view in which another aspect of the piercer is viewed from obliquely above.
Figure 34B:
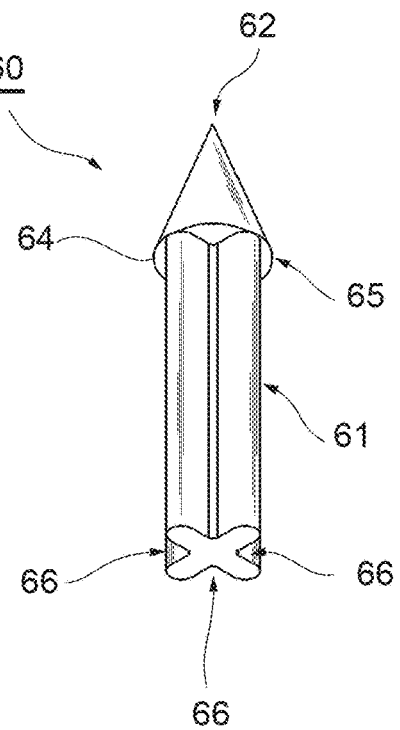
FIG. 34B shows a perspective view in which the same is viewed from obliquely below.
Figure 35:
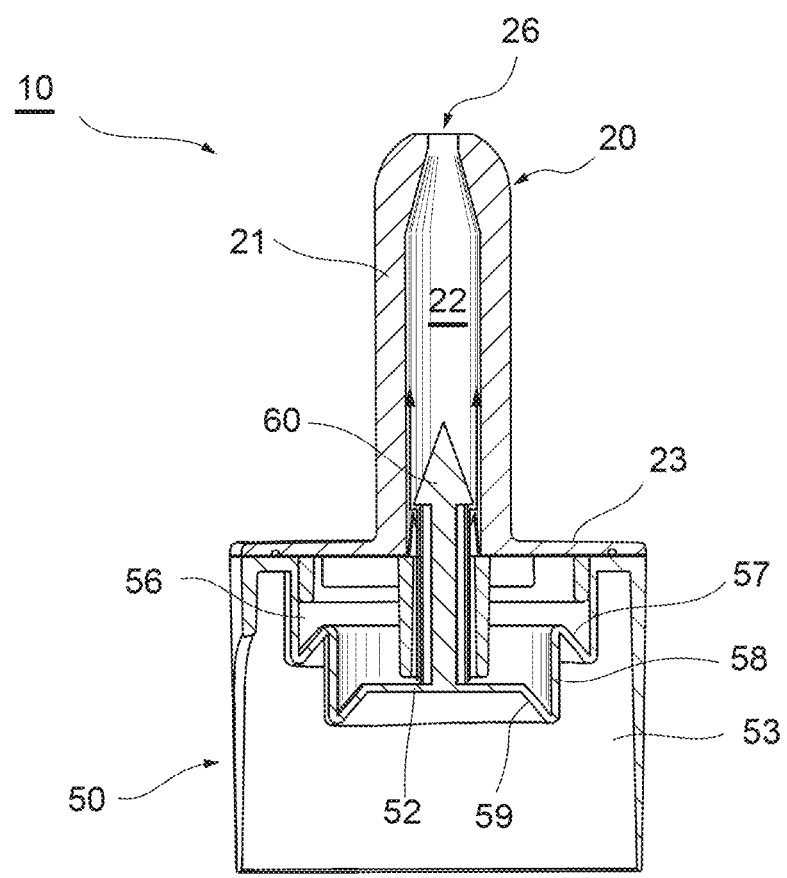
FIG. 35 is a vertical cross-sectional view for explaining a flow of air around the piercer that is obtained immediately after a hole is formed by puncturing in the sealing member with the piercer shown in FIGS. 34A and 34B.
Figure 36:
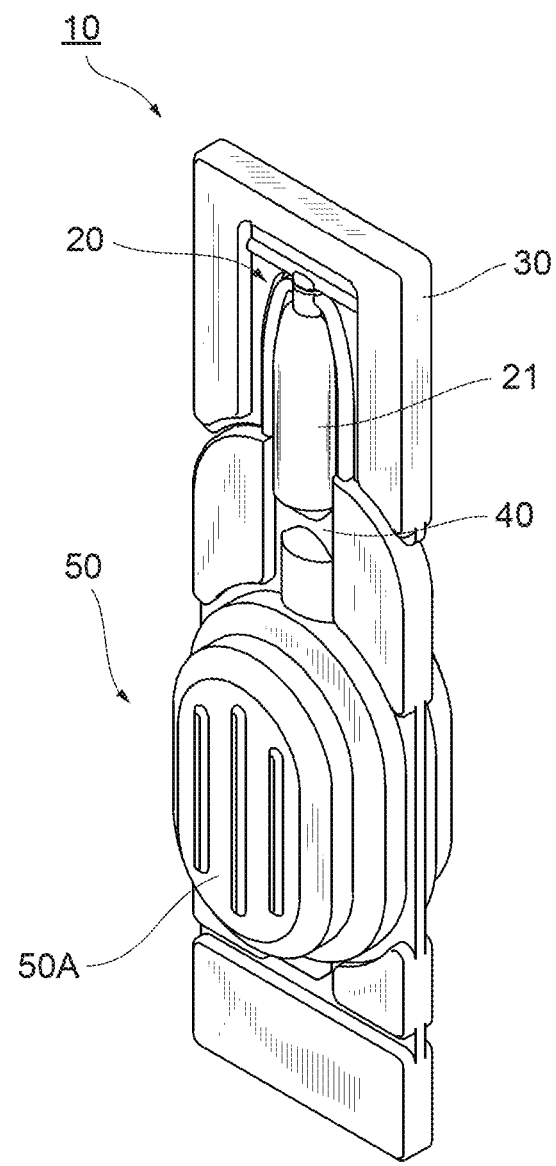
FIG. 36 is a perspective view of the intranasal delivery device for powdered medicine (medicine dispensing device) according to a fifth embodiment of the present invention.

According to another aspect, the piercer 60 that includes the tip portion 62, the cap portion 64, the edge portion 65, and the groove portions 66 may be adopted (see FIGS. 34A, 34B and 35). Note that the description of the piercer 60 partially overlaps with that of the first embodiment and is therefore omitted accordingly.

Fifth Embodiment

The medicine dispensing device (also called "intranasal delivery device for powdered medicine") 10 according to a fifth embodiment of the present invention is now described hereinafter (see FIGS. 36 to 41B).

Characteristics [1] to [6] of the intranasal delivery device for powdered medicine 10 according to the present embodiment are simply described hereinafter, and thereafter the structure and the like of the same are described.

[1. Improved Uniformity of Each Dose]
Injector that also functions as a container is filled in advance with a single dose of medicine.
<<Compressed air flows into the nozzle at once, generating a high-speed airflow, thereby improving the efficiency of injection of the formulation inside the nozzle.>>
<<The rectifying effect of the structure of a peeler tip improves the efficiency of injection of the formulation inside the nozzle.>>

Injection characteristics are less dependent on operation methods.

<<When the pressure of the air inside the pump reaches a certain level or higher as a result of pushing the pump, the air with certain characteristics flows into the nozzle by peeling off a weak sealing portion or by the peeler tip peeling off the weak sealing portion.>>

<<By adding a mechanism that needs to break a joint portion or release a coupling portion at the start of the activation of the peeler, the step of pushing the pump to the end with the force acting to break the joint portion or release the coupling portion is further enhanced, thereby increasing the probability that the air with certain characteristics will flow into the nozzle.>>

[2. Improvement in Storage Stability of Medicine]

The container is sealed until immediately before administration.

[3. Simplification of Administration Operation]

Simple operation.

<<No need to load the injector with a container containing a medicine.>>

<<The pump is pressed only once.>>

[4. Improved Portability]

Downsizing.

[5. Increased Productivity by Reducing the Number of Parts (Leading to Cost Reduction)]

Minimum of one part by application of blow molding and thermocompression bonding (without the peeler part).

[6. Misoperation Prevention Function]

By adding the mechanism that needs to break the joint portion or release the coupling portion at the start of the activation of the peeler, the pump is prevented from being accidentally pushed when no force is required to break the joint portion or release the coupling portion.

The structure and the like of the intranasal delivery device for powdered medicine 10 are described hereinafter with reference to the drawings. The intranasal delivery device for powdered medicine 10 of the present embodiment includes the nozzle member 20, the tab 30, the sealing member 40, the pump member 50, and the like (see FIG. 36 and the like).

The nozzle member 20 is a cylindrical member provided with an appropriate level of roundness so as to facilitate the administration of a powdered medicine into a nasal cavity of a patient. The filling space 22 that is filled with a medicine is formed inside the cylindrical portion 21 of the nozzle member 20 (see FIGS. 21, 22, and the like). The ejection opening 26 is provided at the tip of the nozzle member 20.

Figure 37:
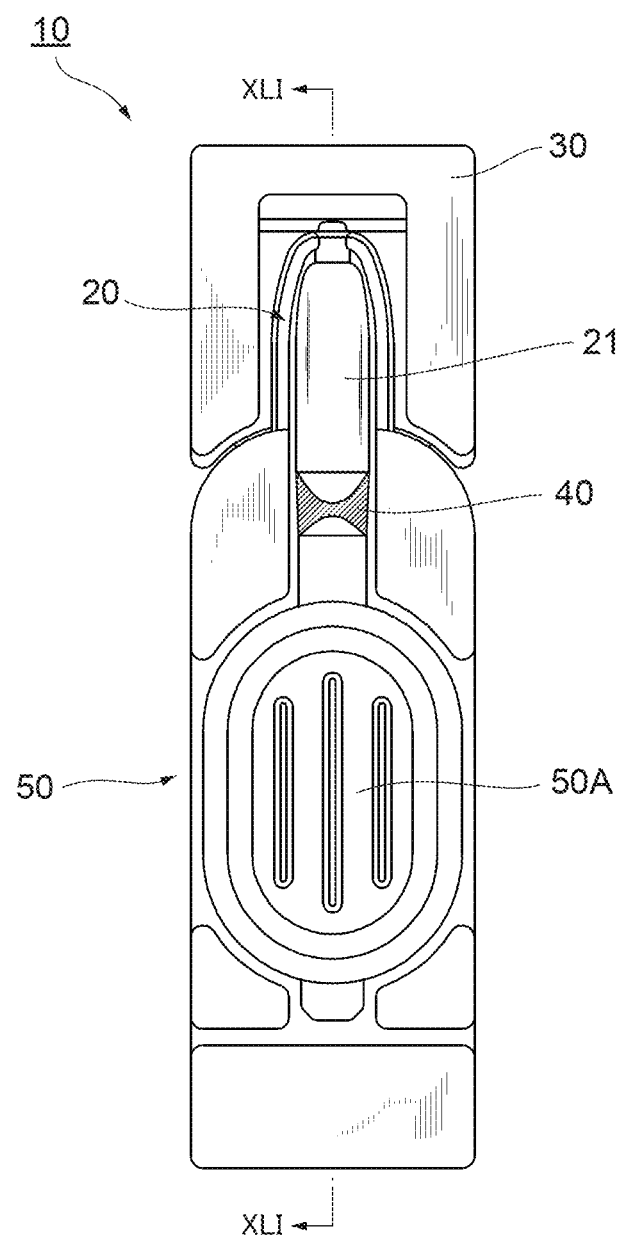
FIG. 37 is a front view of the intranasal delivery device for powdered medicine.
Figure 38:
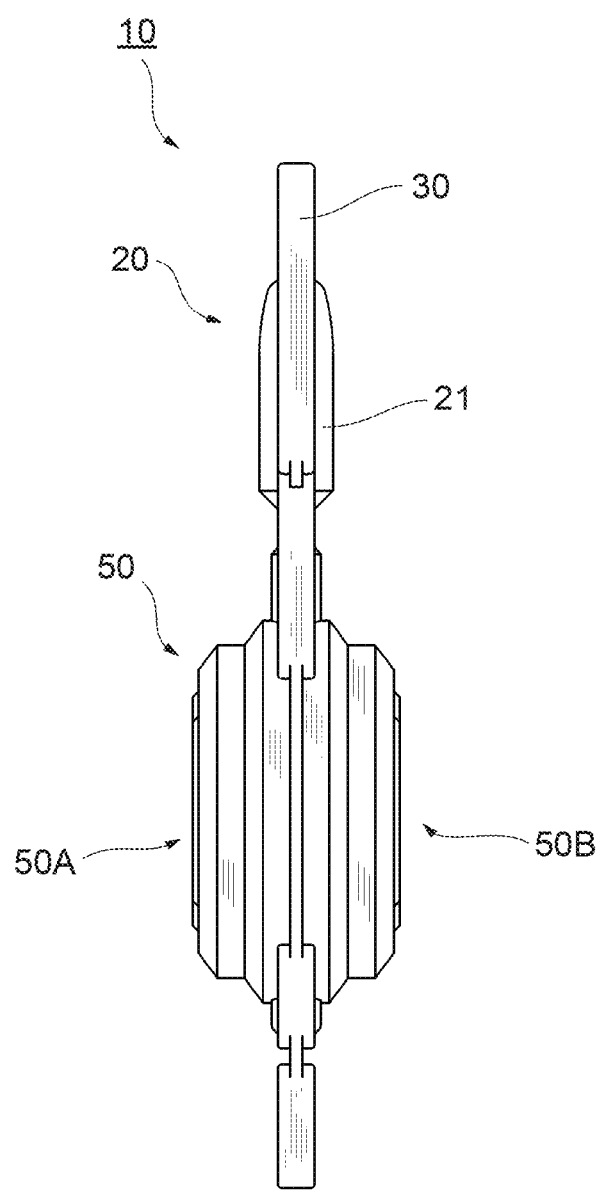
FIG. 38 is a right side view of the intranasal delivery device for powdered medicine.
Figure 39:
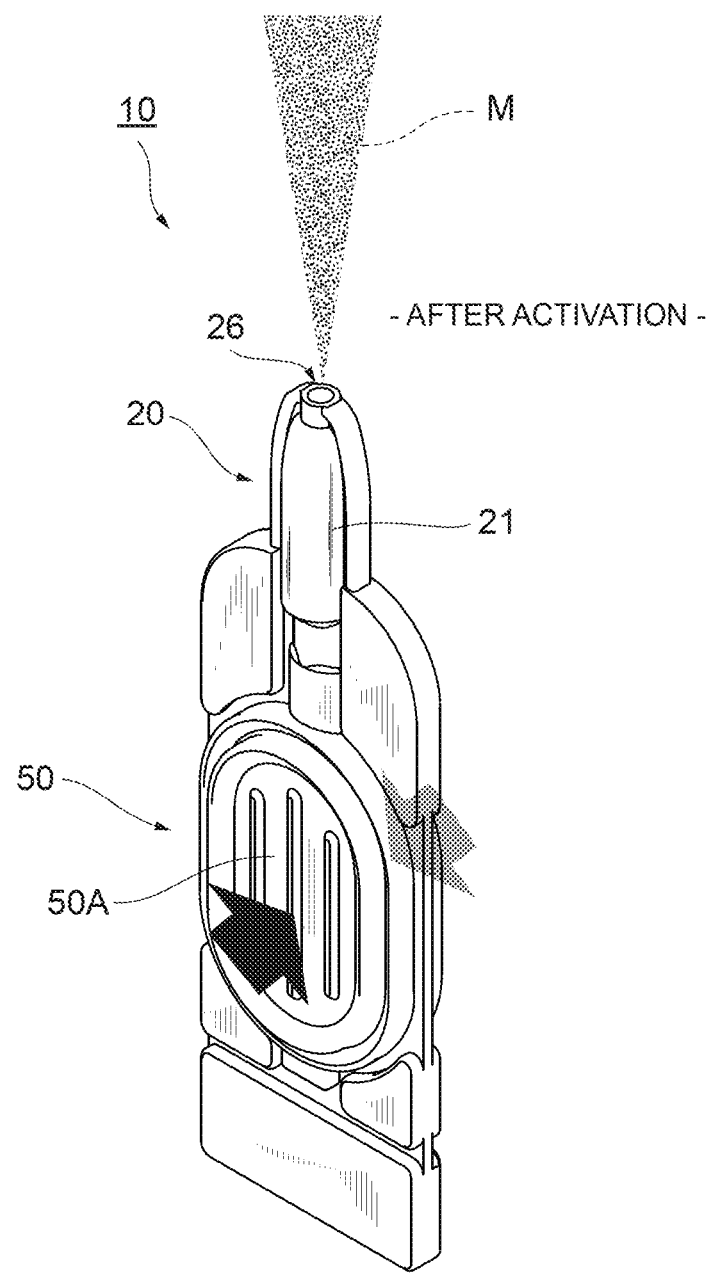
FIG. 39 is a perspective view of the intranasal delivery device for powdered medicine during or after activation thereof.
Figure 40:
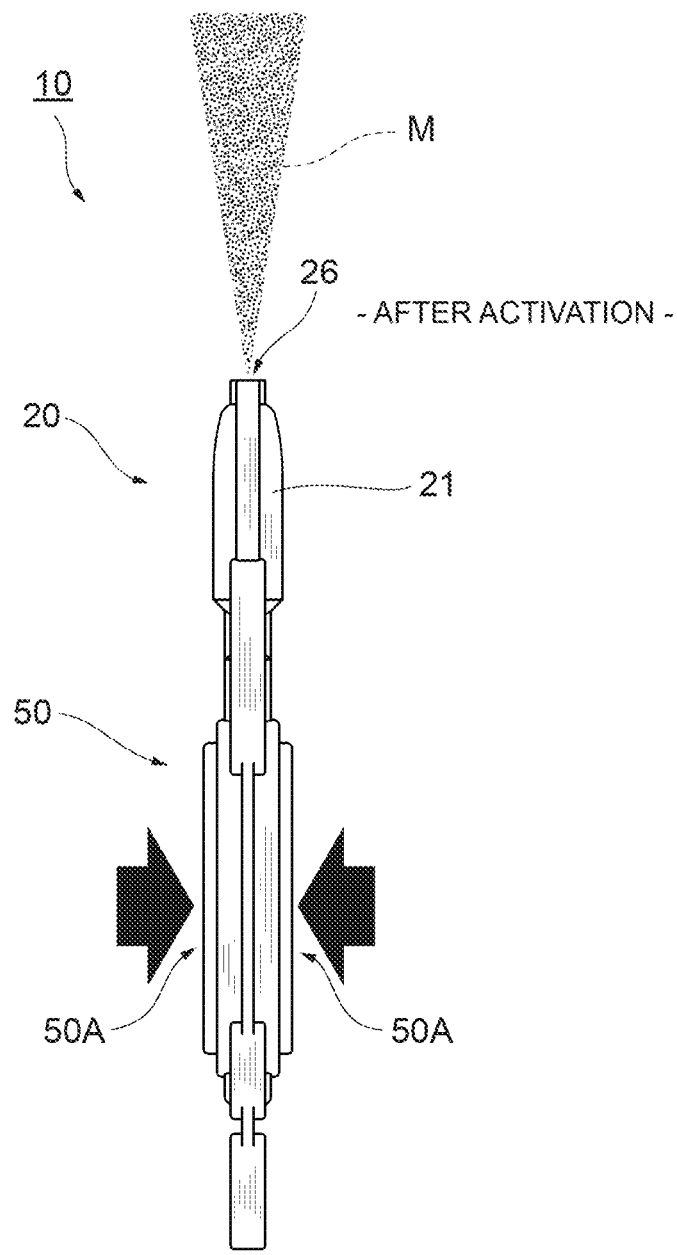
FIG. 40 is a right side view of the intranasal delivery device for powdered medicine during or after activation thereof.

The tab 30 is a member (closing member) for closing the ejection opening 26 of the nozzle member 20 and is attached in a breakable manner so as to cover the nozzle member 20 (see FIG. 37 and the like). At the time of use, the user breaks off the tab 30 with a hand to open the ejection opening 26 (see FIGS. 42A, 42B and the like).

Figures 41A, 41B:
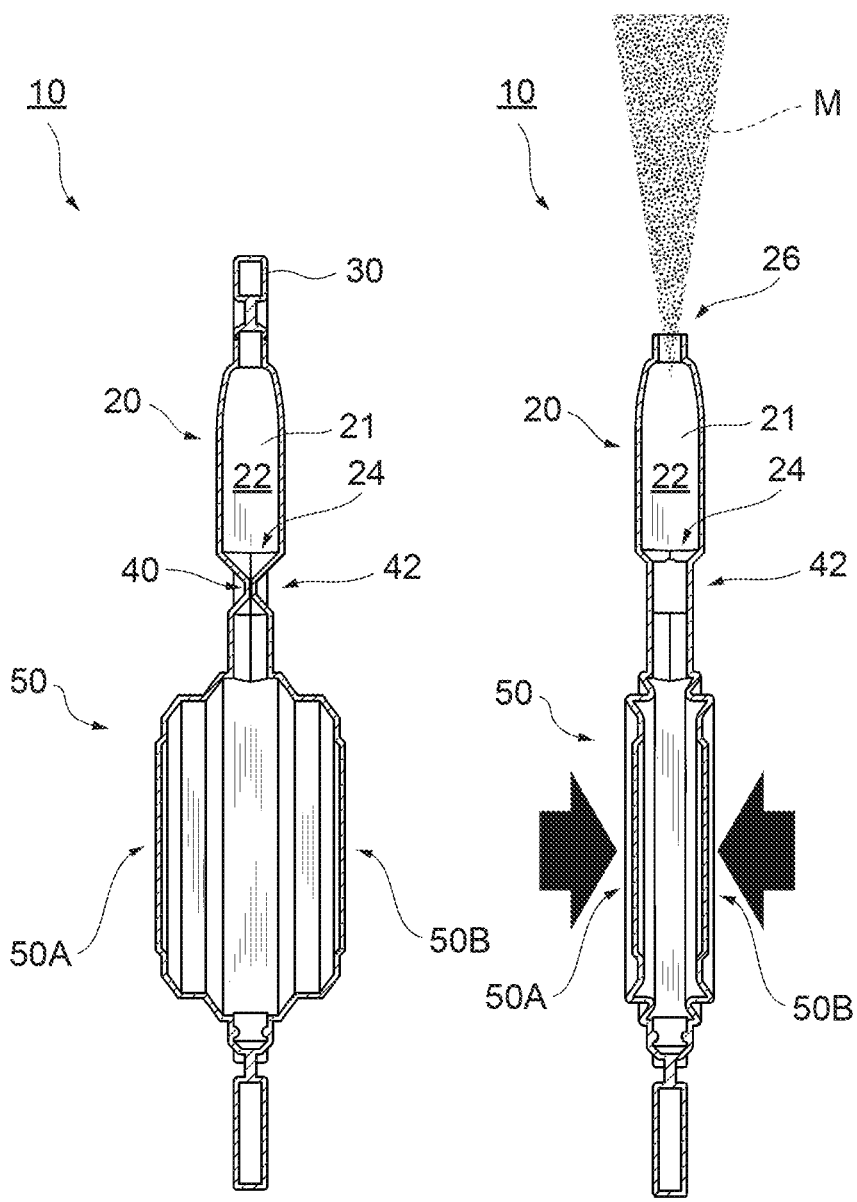
FIG. 41A shows a cross-sectional view of the device for delivering a powdered medicine into the nasal cavity, taken along XLI-XLI of FIG. 37.
FIG. 41B shows a cross-sectional view of the intranasal delivery device for powdered medicine during or after activation thereof.

The sealing member 40 is a member for sealing the opening 24 of the filling space 22 of the nozzle member 20, and is formed in, for example, a flow passage between the nozzle member 20 and the pump member 50 (shown by reference numeral 42 in FIGS. 41A, 41B and the like). The present embodiment adopts the sealing member 40 having weak sealing properties that peels off and releases the sealed state thereof when or before the air pressure in the pump member 50 rises to a positive pressure equal to or greater than a predetermined value as a result of pushing the pump member 50. Such sealing member 40 is formed by using means such as high frequency welding, thermocompression bonding, or ultrasonic welding.

The pump member 50 is a member that feeds air to eject the powdered medicine M from the ejection opening 26 of the nozzle member 20 when the intranasal delivery device for powdered medicine 10 is being used. The pump member 50 of the present embodiment expands in the direction perpendicular to the direction in which the powdered medicine M is ejected from the nozzle member 20 (for example, the front direction (on the viewer's left side) and the rearward direction (on the viewer's right side) in FIG. 38), wherein the expanded surface has a flat shape, and the pump member 50 also includes pressing portions 50A, 50B that are in pairs on the front and back. The pump member 50 is configured to contract and collapse when the user pushes these opposing pressing portions 50A, 50B with his/her finger (see FIGS. 41A, 41B and the like).

Sixth Embodiment

The intranasal delivery device for powdered medicine 10 according to the fifth embodiment may further include an unsealing member 90 that operates in response to an operation by the user and releases the sealed state of the opening 24. Hereinafter, mainly the differences between the intranasal delivery device for powdered medicine 10 of the fifth embodiment and the intranasal delivery device for powdered medicine 10 of the sixth embodiment are described (see FIGS. 42A, 42B and the like).

The unsealing member (also referred to as "peeler", hereinafter) 90 provided in the intranasal delivery device for powdered medicine 10 is a member that is built into the pump member 50, elongates as the pump member 50 contracts, and comes into contact with the sealing member 40 while elongating, to release the sealed state of the opening 24. A tip portion 91 of the peeler 90 has a tapered shape suitable for enlarging or peeling the sealing member 40 to release the sealed state thereof (see FIGS. 42A, 42B and the like).

In addition to the tip portion 91 described above, the peeler 90 of the present embodiment also has a base end portion 92, a deformed portion 93, and pressed portions 94 (see FIGS. 42A, 42B and the like). The base end portion 92 is a portion located on the opposite side (base end side) of the ejection opening 26, and a part of the base end portion 92 is heat-welded to the pump member 50. The deformed portion 93 is a pantograph-shaped portion composed of four pieces arranged into a diamond shape, collapses as the pump member 50 contracts, and elongates by $\Delta D$ ($=D2-D1$) toward the ejection opening 26 (see FIGS. 43 and 44). The pressed portions 94 are each, for example, a plate-shaped member disposed inside the pressing portions 50A, 50B of the pump member 50, and transmits the force of the finger of the user pressing the pressing portions 50A, 50B, to the deformed portion 93 (FIG. 45 and the like).

Figure 43:
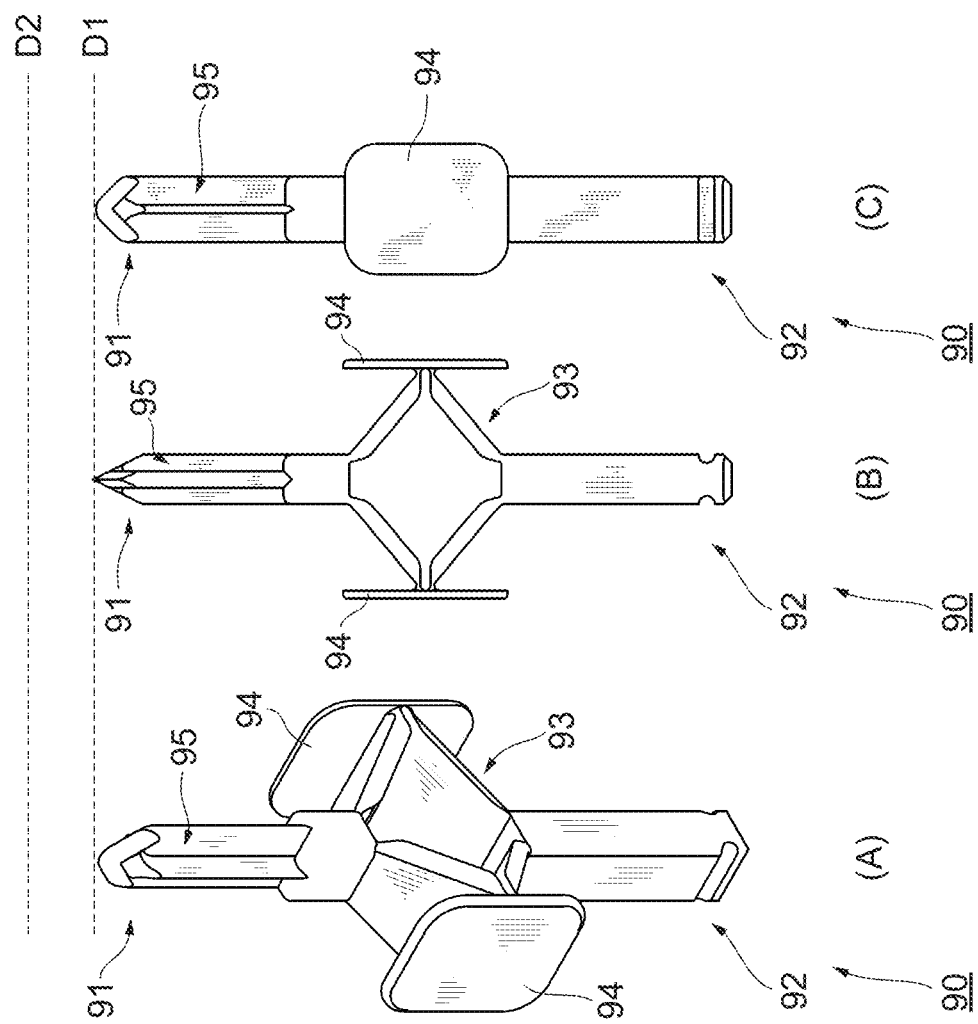
FIG. 43 shows (A) a perspective view, (B) a front view, and (C) a side view of a peeler (unsealing member) according to the sixth embodiment of the present invention.
Figure 44:
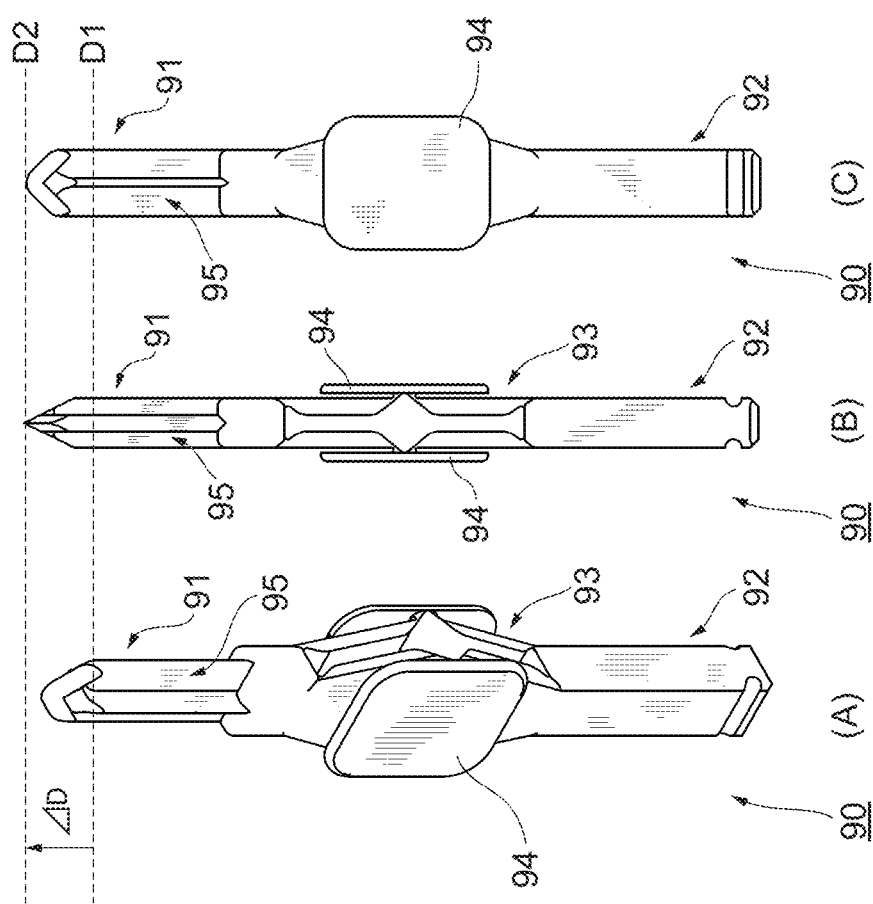
FIG. 44 shows (A) a perspective view, (B) a front view, and (C) a side view of the peeler that is elongated.
Figure 45:
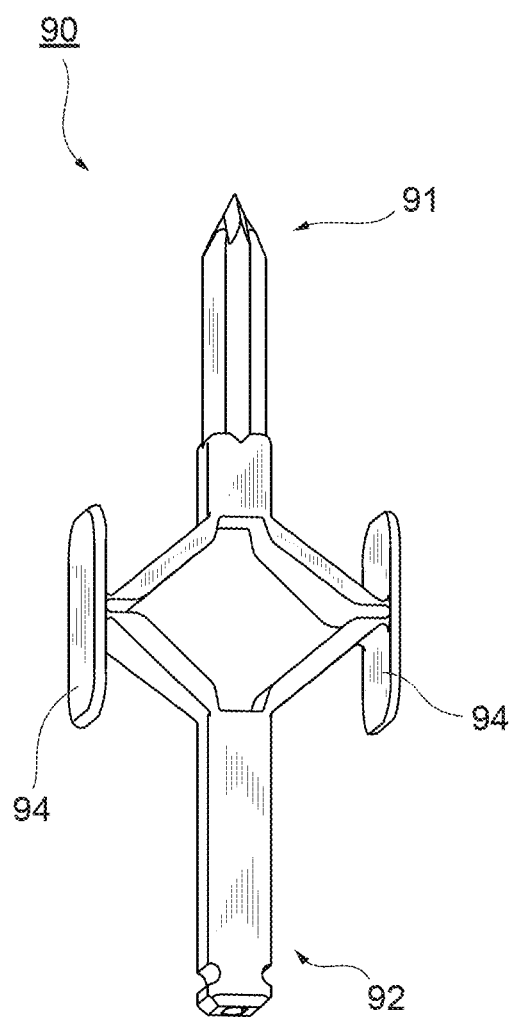
FIG. 45 is an overall perspective view of the peeler.

A groove 95 to make rectification may be provided at the tip portion 91 of the peeler 90 (see FIGS. 43 to 45). By rectification of the groove 95, the powdered medicine M can be diffused more uniformly and discharged evenly.

Note that the peeler 90 of the present embodiment is made of a plastic material, such as a resin material, which does not easily return to the original shape thereof after being deformed. Thus, the deformed peeler 90 is not restored, and the pump member 50 that has once contracted does not swell up accordingly.

The intranasal delivery device for powdered medicine 10 may further include a guide member that restricts a movement of the peeler 90 in a direction (lateral direction) perpendicular to the direction of the elongation of the peeler 90. For example, in the intranasal delivery device for powdered medicine 10 of the present embodiment, a tubular portion (indicated by reference numeral 25 in FIGS. 42A and 42B) of the nozzle member 20 that is located in the vicinity of the opening 24 functions as the guide member (see FIGS. 42A and 42B). Also, the pressed portions 94 in contact with respective inner surfaces of the pressing portions 50A, 50B of the pump member 50 can also function to restrict the movement of the peeler 90 in the lateral direction.

A function for suppressing an erroneous operation or for pushing the pump member 50 all the way with great force may be added to the intranasal delivery device for powdered medicine 10. Specific examples of a member realizing such function (erroneous operation suppressing member) are as follows (see FIGS. 46 to 48).

Figure 46:
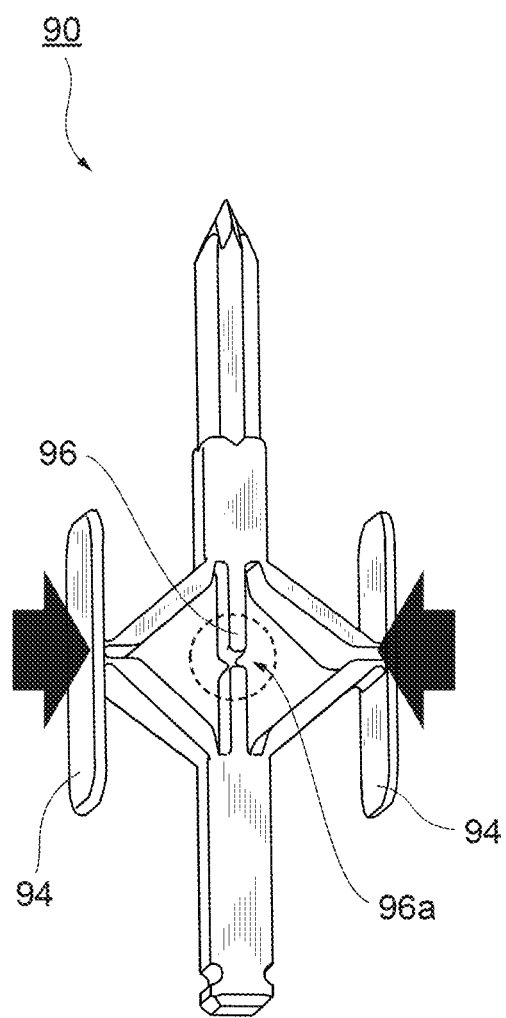
FIG. 46 is an overall perspective view of the peeler, showing a first specific example of an erroneous operation suppressing member provided in the peeler.

A first specific example of an erroneous operation suppressing member 96 is a member that joins the tip portion 91 and the base end portion 92 to each other (see FIG. 46). The middle of the erroneous operation suppressing member 96 is a narrow portion 96a that breaks when the pressed portions 94 are pressed (see the arrows shown in the drawing) and consequently a force acting as a tensile force via the deformed portion 93 reaches a certain level (see the part with the broken line in the drawing). When the erroneous operation suppressing member 96 (the narrow portion 96a thereof) breaks while the tensile force acts, the peeler 90 rises with great force, and the resultant pushing force applied to the pump member 50 pushes the pump member 50 all the way. Also, the movement of the peeler 90 is suppressed until the pushing force applied to the pump member 50 (or the tensile force acting on the erroneous operation suppressing member 96) reaches a certain level, preventing an erroneous operation and malfunction of the intranasal delivery device for powdered medicine 10.

Figure 47:
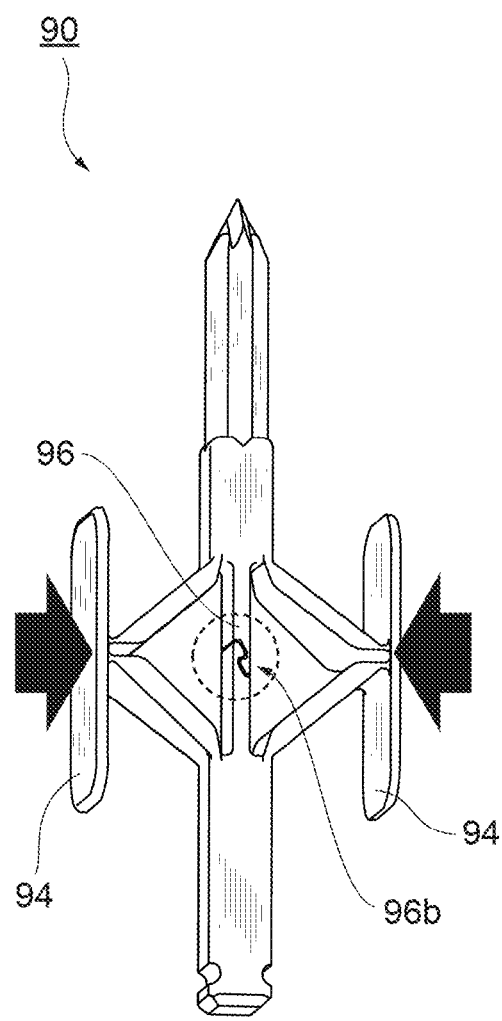
FIG. 47 is an overall perspective view of the peeler, showing a second specific example of the erroneous operation suppressing member provided in the peeler.

A second specific example of the erroneous operation suppressing member 96 is a member that couples the tip portion 91 and the base end portion 92 to each other (see FIG. 47). The middle of the erroneous operation suppressing member 96 is a locking portion 96b that is shaped in a disconnected state, and thereafter meshed and locked to each other to be in a coupled state (see the part with the broken line in the drawing). The locking portion 96b is removed when the pump member 50 is pressed and a tensile force acting on the erroneous operation suppressing member 96 reaches a certain level. The subsequent movement and action are the same as those of the first specific example.

Figure 48:
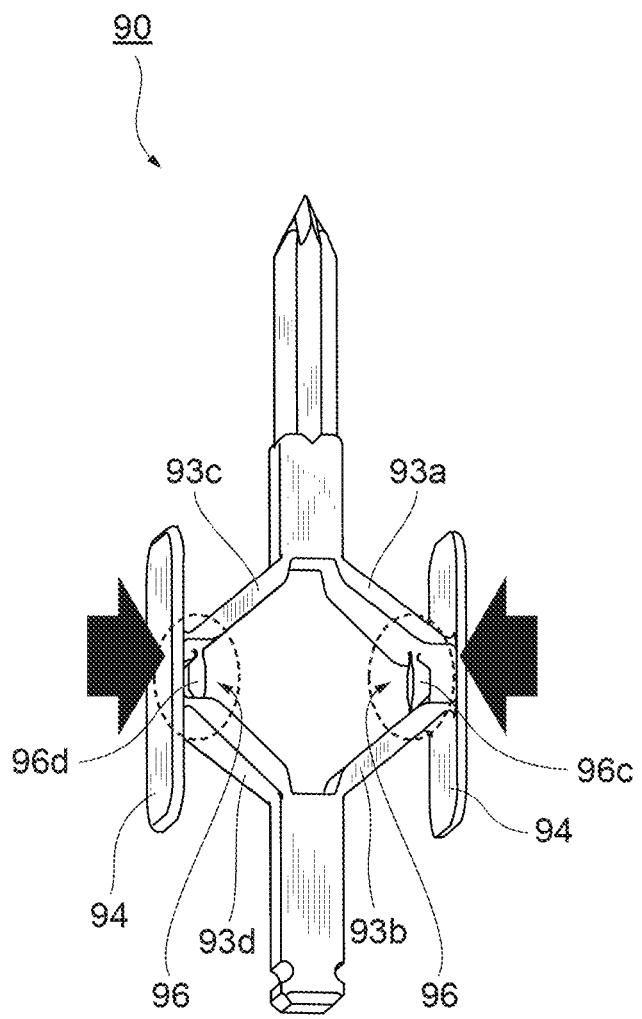
FIG. 48 is an overall perspective view of the peeler, showing a third specific example of the erroneous operation suppressing member provided in the peeler.

A third example of the erroneous operation suppressing member 96 is a member that is composed of a small piece 96c joining an upper right piece 93a and a lower right piece 93b of the deformed portion 93 and/or a small piece 96d joining an upper left piece 93c and a lower left piece 93d of the deformed portion 93 (see FIG. 48). The erroneous operation suppressing member 96 breaks when the pump member 50 is pressed and a tensile force acting on the small piece 96c and/or the small piece 96d reaches a certain level. The subsequent movement and action are the same as those of the first specific example.

Seventh Embodiment

Figure 49:
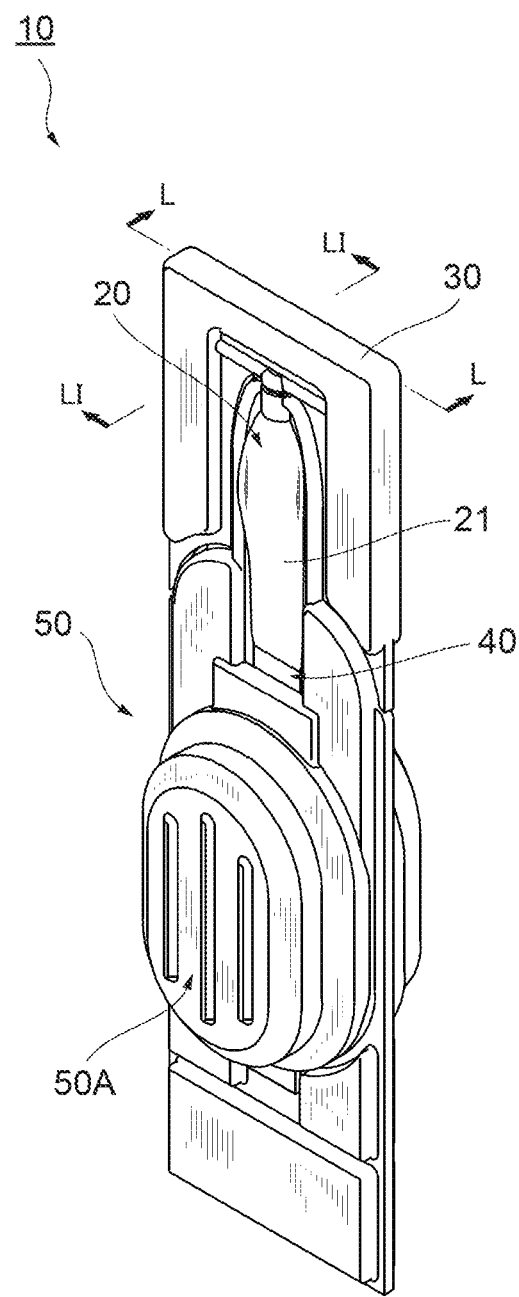
FIG. 49 is a perspective view of the intranasal delivery device for powdered medicine (medicine dispensing device) according to a seventh embodiment of the present invention.
Figure 50:
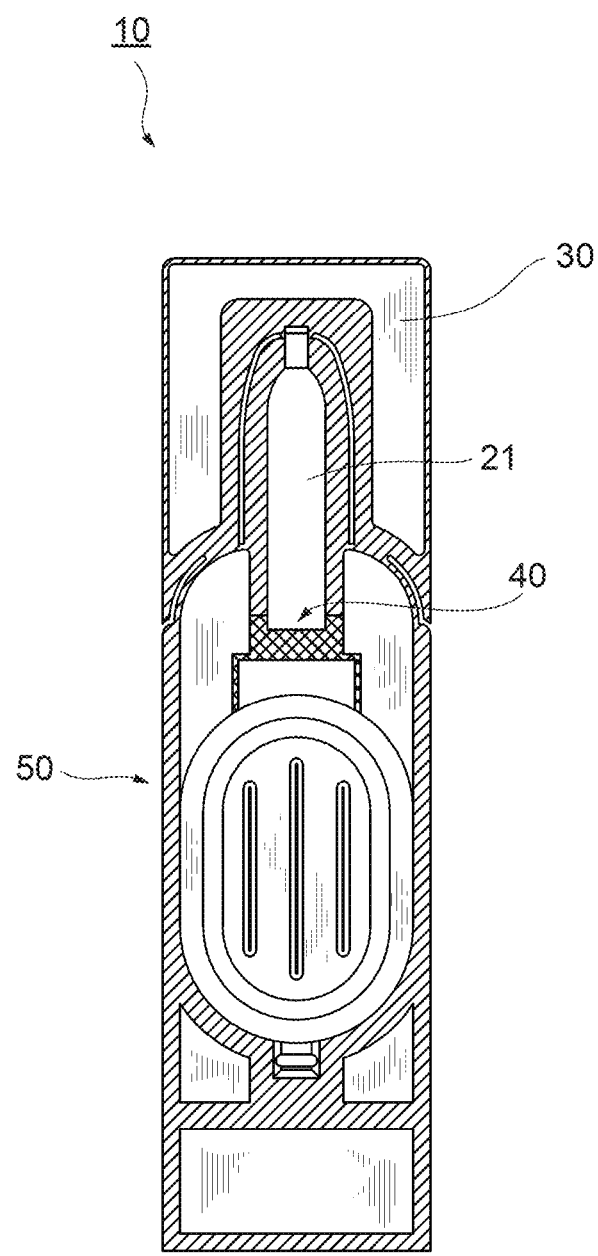
FIG. 50 is a cross-sectional view of the intranasal delivery device for powdered medicine, taken along line L-L of FIG. 49.
Figure 51:
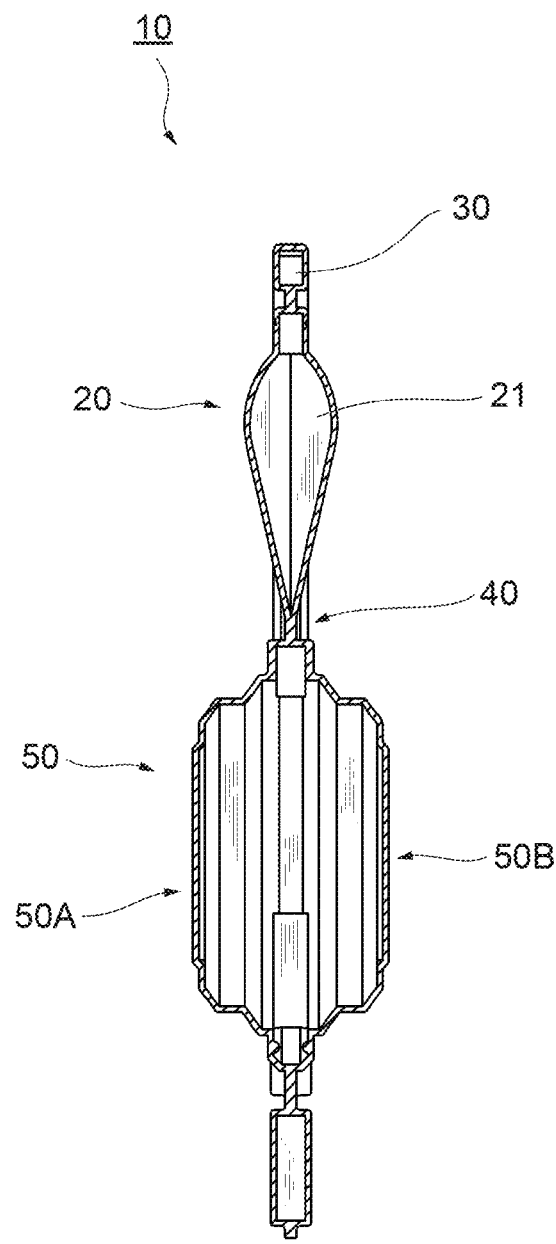
FIG. 51 is a cross-sectional view of the intranasal delivery device for powdered medicine, taken along line LI-LI of FIG. 49.
Figure 52:
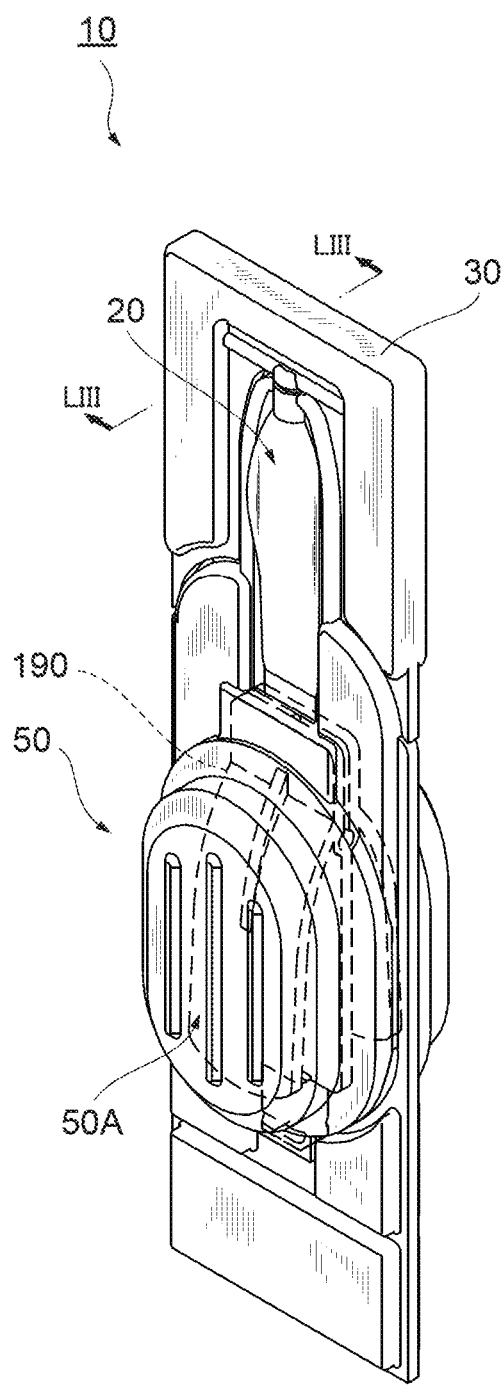
FIG. 52 is a perspective view of the device for delivering a powdered medicine into the nasal cavity (medicine dispensing device) according to an eighth embodiment of the present invention.

In the intranasal delivery device for powdered medicine 10 described in the fifth embodiment, the nozzle member 20 has a shape in which the part in the vicinity of the tip thereof is rounded and expanded (see FIGS. 49 to 51).

Eighth Embodiment

The intranasal delivery device for powdered medicine 10 described in the seventh embodiment may further include a peeler (unsealing member) 190 that opens in response to an operation by the user and releases the sealed state of the opening 24. The peeler 190 is described hereinafter as an eighth embodiment (see FIGS. 52 to 57).

Figure 53:
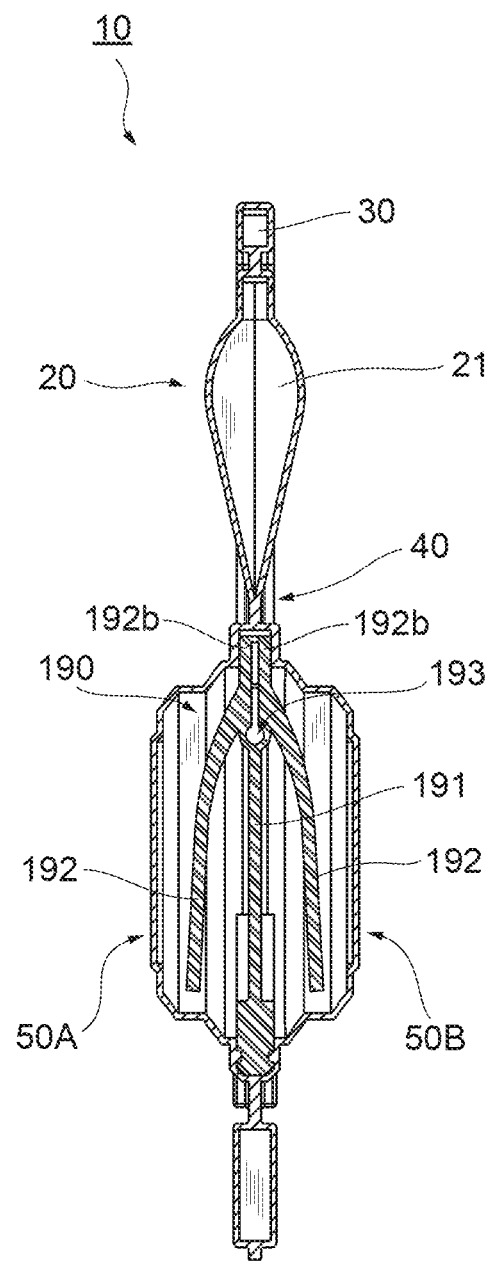
FIG. 53 is a cross-sectional view of the intranasal delivery device for powdered medicine, taken along LIII-LIII of FIG. 52.
Figure 54:
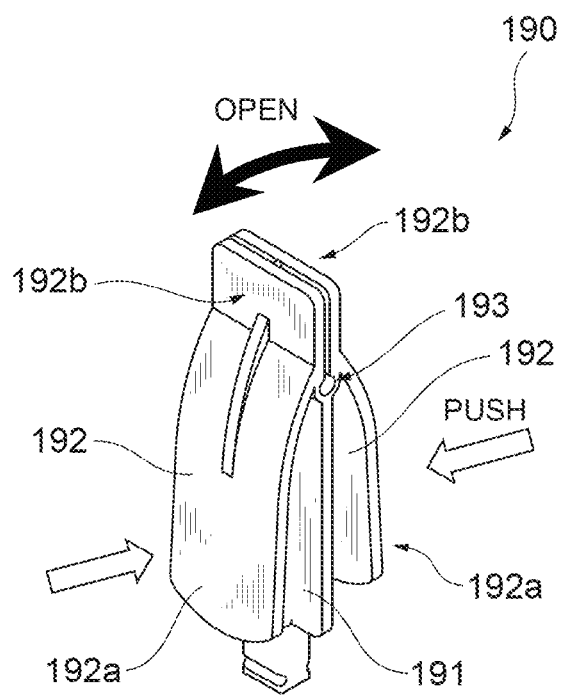
FIG. 54 is a perspective view of the peeler (unsealing member).
Figure 55:
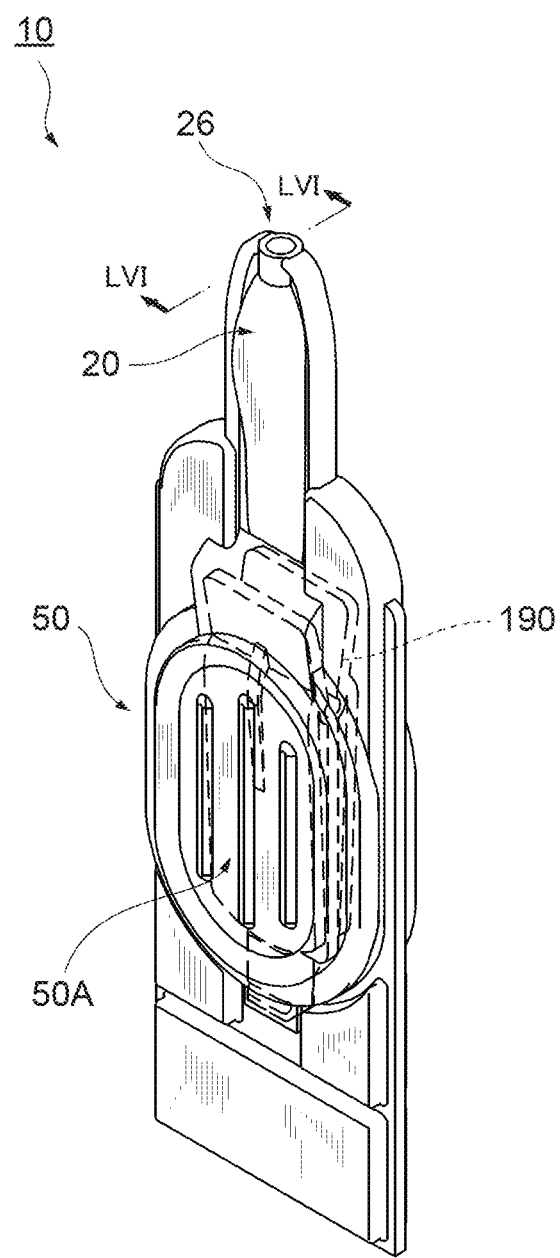
FIG. 55 is a perspective view of the intranasal delivery device for powdered medicine (medicine dispensing device) after activation thereof.
Figure 56:
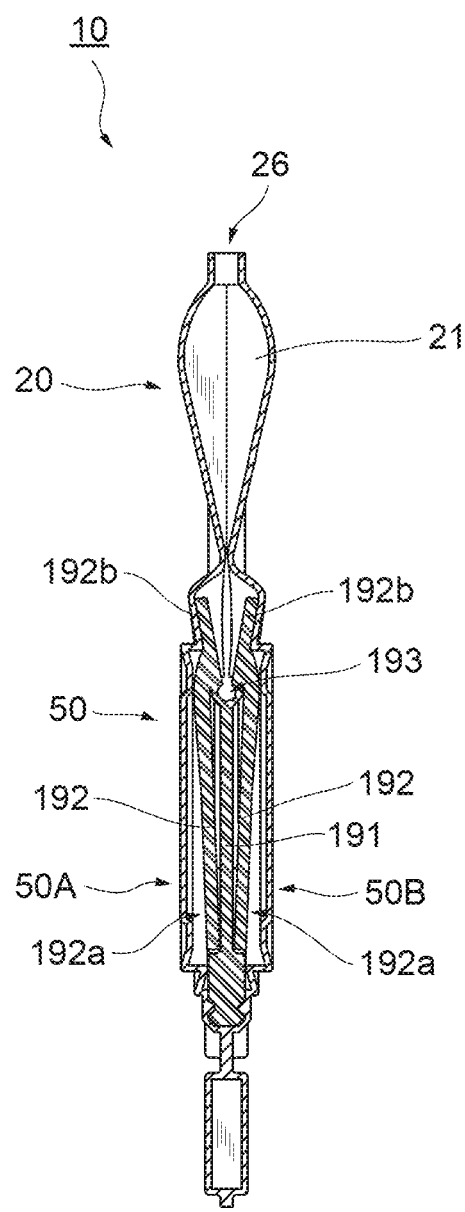
FIG. 56 is a cross-sectional view of the intranasal delivery device for powdered medicine, taken along line LVI-LVI of FIG. 55.
Figure 57:
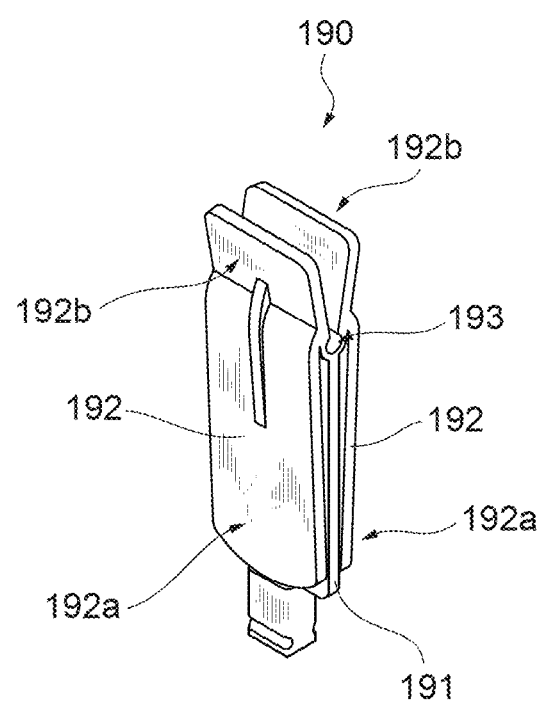
FIG. 57 is a perspective view of the peeler (unsealing member) after activation thereof.

The peeler 190 of the present embodiment is a member that is configured by attaching a pair of plate-like movable members 192 so as to be rotatable about a spindle 193 on a base material 191 as in a clothespin, the peeler 190 being built into the pump member 50 (see FIGS. 53 and 54). When the user presses the pump member 50, a force is applied to pressed portions (points of force) 192a of the respective movable members 192, and as a result, the movable members 192 rotate about the spindle 193, and upper ends (points of action) 192b open, separating the sealing member 40 (see FIGS. 55 to 57 and the like).

Ninth Embodiment

An example of the method for manufacturing the intranasal delivery device for powdered medicine 10 is now described hereinafter as a ninth embodiment of the present invention (see FIGS. 58A to 58E).
<Blow Molding Process>
The peeler 90 is introduced into a tubular parison (outer portion) 12 (see FIG. 58A), which is then blow-molded using a blow die (not shown) (see FIGS. 58A and 58B). In a case where the sealing member 40 having weak sealing properties described in the fifth embodiment is employed, said sealing member 40 can be molded in conjunction with this process.
<Medicine Filling Process>
The filling space 22 of the nozzle member 20 is filled with the powdered medicine M (see FIG. 58D).
<Thermocompression Bonding/Final Molding Process>
The part of the nozzle member 20 in the vicinity of the ejection opening 26 is sealed by thermocompression bonding, and thereafter subjected to final molding (see FIG. 58E).

Although blow molding has been described above as the manufacturing method, blow molding is merely a favorable example. The parison 12 can be molded by blow molding, injection molding, or vacuum molding.

Although "intranasal delivery device for powdered medicine 10" has been described in the first to ninth embodiments, the intranasal delivery device for powdered medicine 10 is merely a favorable specific example of a single-use medicine dispensing device according to the present invention. The medicine dispensing device is applicable in addition to a nasal cavity.

INDUSTRIAL APPLICABILITY

The present invention is suitable for application to a variety of nasal medicine dispensing devices and the like.

What is claimed is:

1. A medicine dispensing device of a single-use type for dispensing a predetermined dose of a powdered medicine into a nasal cavity, the medicine dispensing device comprising:
   a nozzle member that includes a filling space to be filled with the powdered medicine and an ejection opening from which the powdered medicine is ejected;
   a closing member that closes the ejection opening;
   a sealing member that seals an opening on a side opposite to the ejection opening of the filling space;
   a pump member configured to expel air as the pump member contracts by pressure on a bottom portion of the pump member, to eject the powdered medicine from the ejection opening;
   a puncturing member comprising a tip portion having a conical shape configured to form a hole by puncturing the sealing member, the puncturing member being configured to move toward the sealing member as the pump member contracts; and
   a cap portion formed on an underside of the tip portion of the puncturing member and configured to direct air flowing through the hole of the sealing member in a radially outward direction.

2. The medicine dispensing device according to claim 1, wherein the pump member is configured to plastically deform after contracting.

3. The medicine dispensing device according to claim 1, wherein the sealing member is unsealed when a positive pressure is applied.

4. The medicine dispensing device according to claim 1, wherein the sealing member is configured to peel at a predetermined pressure applied by the pump member as the pump member contracts.

5. The medicine dispensing device according to claim 1, wherein the puncturing member further comprises a groove portion extending along a direction of movement of the puncturing member as the pump member contracts.

6. The medicine dispensing device according to claim 5, wherein a plurality of groove portions are formed on a shaft portion of the puncturing member.

7. The medicine dispensing device according to claim 6, wherein the cap portion is inclined such that the cap portion gradually approaches the tip portion in a radially inward direction toward the shaft portion of the puncturing member.

8. The medicine dispensing device according to claim 7, wherein the cap portion is inclined in a shape of an umbrella.

9. The medicine dispensing device according to claim 7, wherein the cap portion is flat.

10. The medicine dispensing device according to claim 9, wherein a base portion of a puncturing member is in contact with the bottom portion of the pump member.

11. The medicine dispensing device according to claim 1, further comprising a guide member that restricts the puncturing member from moving in a direction perpendicular to a direction of movement of the puncturing member as the pump member contracts.

12. The medicine dispensing device according to claim 11, wherein a base end portion of the puncturing member is in contact with the bottom portion of the pump member.

13. The medicine dispensing device according to claim 12, wherein the pump member has a tapered shape that narrows downward from the nozzle member side toward the bottom portion of the pump member.

14. The medicine dispensing device according to claim 13, comprising a finger hook portion configured to receive a finger of a user when the pump member contracts.

15. The medicine dispensing device according to claim 14, wherein the closing member is disposed such that a portion thereof is located in the finger hook portion and configured such that the user can hook a finger on the finger hook portion by removing the closing member.

16. The medicine dispensing device according to claim 14, further comprising a pump malfunction prevention cover configured to prevent ejection of the powdered medicine from the ejection opening.

17. The medicine dispensing device according to claim 13, further comprising a return motion prevention member configured to prevent the pump member from returning to an original state thereof after contracting.

* * * * *